United States Patent
Kobayashi et al.

(10) Patent No.: US 11,406,831 B2
(45) Date of Patent: Aug. 9, 2022

(54) TERMINAL DEVICE, TREATMENT SYSTEM, AND PROGRAM

(71) Applicant: OMRON HEALTHCARE Co., Ltd., Kyoto (JP)

(72) Inventors: Yuka Kobayashi, Kyoto (JP); Shozo Takamatsu, Kyoto (JP); Tamaki Ito, Kyoto (JP)

(73) Assignee: OMRON HEALTHCARE CO., LTD., Muko (JP)

(*) Notice: Subject to any disclaimer, the term of this patent is extended or adjusted under 35 U.S.C. 154(b) by 31 days.

(21) Appl. No.: 16/705,283

(22) Filed: Dec. 6, 2019

(65) Prior Publication Data

US 2020/0108259 A1 Apr. 9, 2020

Related U.S. Application Data

(63) Continuation of application No. PCT/JP2018/021540, filed on Jun. 5, 2018.

(30) Foreign Application Priority Data

Jun. 7, 2017 (JP) .............................. JP2017-112624

(51) Int. Cl.
*A61N 1/372* (2006.01)
*A61N 1/36* (2006.01)
(Continued)

(52) U.S. Cl.
CPC ....... *A61N 1/37217* (2013.01); *A61N 1/0456* (2013.01); *A61N 1/0464* (2013.01); *A61N 1/3603* (2017.08); *H04W 12/06* (2013.01)

(58) Field of Classification Search
CPC .............. A61N 1/37217; A61N 1/3603; A61N 1/0456; A61N 1/0464; A61N 1/37254;
(Continued)

(56) References Cited

U.S. PATENT DOCUMENTS 9,731,140 B1* 8/2017 Perryman .......... A61N 1/37247
2008/0312512 A1* 12/2008 Brukalo ............ A61M 5/14244
600/300
(Continued)

FOREIGN PATENT DOCUMENTS

JP 2005-237941 A 9/2005
JP 2010278781 A 12/2010
(Continued)

OTHER PUBLICATIONS

International Search Report of the International Searching Authority for PCT/JP2018/021540 dated Sep. 4, 2018.
(Continued)

*Primary Examiner* — Alyssa M Alter
(74) *Attorney, Agent, or Firm* — Birch, Stewart, Kolasch & Birch, LLP

(57) ABSTRACT

A terminal device includes: an information storage that stores registration information for establishing a wireless communication connection with an electrical treatment device; a detection unit that detects a beacon signal emitted from the electrical treatment device; a determination unit that determines, on the based on the registration information stored in the information storage unit and the beacon signal detect, whether the electrical treatment device includes an unregistered electrical treatment device. In a case where the unregistered electrical treatment device is included, the determination unit further determines, on the basis of the beacon signal detected, whether the unregistered electrical treatment device includes registration information of a device other than the terminal device. The terminal device further includes a notification unit that provides notification on information including a solution for an error when the electrical treatment device not registered with the terminal
(Continued)

device includes the registration information of the device other than terminal device.

8 Claims, 18 Drawing Sheets

(51) Int. Cl.
    *A61N 1/04*         (2006.01)
    *H04W 12/06*     (2021.01)

(58) Field of Classification Search
    CPC .... A61N 1/37247; A61N 1/0492; A61N 1/08; A61N 1/36; H04W 12/06; H04W 12/50
    See application file for complete search history.

(56) References Cited

U.S. PATENT DOCUMENTS

| | | | |
|---|---|---|---|
| 2009/0299438 A1* | 12/2009 | Nolan | A61N 1/37211 607/60 |
| 2012/0069792 A1 | 3/2012 | Kishida | |
| 2014/0135880 A1 | 5/2014 | Baumgartner et al. | |
| 2015/0073498 A1 | 3/2015 | Kothandaraman | |
| 2015/0089590 A1* | 3/2015 | Krishnan | H04L 63/08 726/3 |
| 2016/0082273 A1 | 3/2016 | Baumgartner et al. | |
| 2016/0307012 A1* | 10/2016 | Narasimha | H04B 5/0062 |
| 2016/0330573 A1* | 11/2016 | Masoud | G06F 21/606 |
| 2019/0159738 A1* | 5/2019 | Murai | G06Q 50/22 |
| 2019/0363568 A1* | 11/2019 | Fyfe | B62J 45/40 |

FOREIGN PATENT DOCUMENTS

| | | |
|---|---|---|
| JP | 2016506097 A | 2/2016 |
| JP | 2016534821 A | 11/2016 |

OTHER PUBLICATIONS

Translation of the International Search Report of the International Searching Authority for PCT/JP2018/021540 dated Sep. 4, 2018.
Office Action dated Sep. 13, 2021 in corresponding German Patent Application No. 11 2018 002 371.0, with English translation.

* cited by examiner

TERMINAL DEVICE, TREATMENT SYSTEM, AND PROGRAM

CROSS-REFERENCE TO RELATED APPLICATIONS

This is a continuation of International Applications PCT/JP2018/021540, with an international filing date of Jun. 5, 2018, and 2017-112624, with an international filing date of Jun. 7, 2017, filed by applicant, the disclosure of which is hereby incorporated by reference in its entirety.

TECHNICAL FIELD

The present disclosure relates to a terminal device, a treatment system, and a program, with the terminal device being configured to wirelessly communicate with an electrical treatment device.

BACKGROUND ART

A known electrical treatment device provides electrical stimulation by outputting a low-frequency pulse to muscles within the body via a plurality of pads attached to the surface regions of the body, such as the abdomen and the back. In recent years, various processes have been performed by devices that perform wireless communication with such electrical treatment devices.

For example, JP 2016-506097 T (Patent Document 1) describes a system for wireless pairing and communication for electrical stimulation. The system includes pairing two or more devices into a network configuration using, in part, a pairing device. The system also includes partially using one or more electrical stimulation contacts for electrical stimulation therapy and transmitting data between two or more devices by partially using the one or more electrical stimulation contacts for transmitting data between the two or more devices.

JP 2005-237941 A (Patent Document 2) describes a treatment device that is a cordless pulsed current-type health device including a control device and a treatment electrode. The treatment electrode includes a conductive pad configured to come into contact with a skin surface; a pulse current supply portion that receives a supply of power from a power source and supplies a pulse current to the conductive pad; a receiving unit and an antenna that wirelessly receive a control signal transmitted from the control device; and a memory and a CPU that control the operation of the pulse current supply portion according to the control signal.

CITATION LIST

Patent Literature

Patent Document 1: JP 2016-506097 T
Patent Document 2: JP 2005-237941 A

SUMMARY OF INVENTION

Technical Problem

For electrical treatment devices to help with recovery from fatigue, alleviation of muscle pain, and the like, an appropriate electrical stimulation must be provided to the user's body. In other words, an inappropriate electrical stimulation to the user's body may worsen the user's physical condition. Thus, in a case of using a wireless communication connection between an electrical treatment device and a control device, security needs to be sufficiently ensured so that the control of the electrical treatment device by the control device is not taken over.

Patent Document 1 describes a configuration in which a device (for example, an electrical stimulation device) and a pairing device communicate wirelessly. Patent Document 2 describes a configuration in which a control device and a treatment electrode communicate wirelessly. However, in Patent Documents 1 and 2, there is no teaching or suggestion of technology related to the security.

In light of the foregoing, an object of an aspect of the present disclosure is to provide a terminal device, a treatment system, and a program relating to electrical treatment devices communicating wirelessly with the terminal device, which allow security to be easily improved.

Solution to Problem

According to an embodiment, a terminal device is provided that is configured to wirelessly communicate with at least one electrical treatment device. The terminal device includes:

an information storage unit that stores registration information for establishing a wireless communication connection with the at least one electrical treatment device;

a detection unit that detects a beacon signal emitted from the at least one electrical treatment device; and a determination unit that determines, on the basis of the registration information stored in the information storage unit and the beacon signal detected, whether the at least one electrical treatment device includes an unregistered electrical treatment device not registered with the terminal device. When the unregistered electrical treatment device is included, the determination unit further determines, on the basis of the beacon signal detected, whether the unregistered electrical treatment device comprises registration information of a device other than the terminal device. The terminal device further includes a notification unit that provides notification on information including a solution for an error, when the unregistered electrical treatment device comprises the registration information of the device other than the terminal device.

Preferably, when the unregistered electrical treatment device is emitting a beacon signal including a connection request for establishing a wireless communication connection, the determination unit determines that the unregistered electrical treatment device includes the registration information of the device other than the terminal device.

Preferably, the determination unit further determines, on the basis of the beacon signal detected, whether a first classification to which the unregistered electrical treatment device belongs matches a second classification to which an electrical treatment device registered with the terminal device belongs. The notification unit notifies that the unregistered electrical treatment device will not be registered, when the first classification and the second classification do not match.

Preferably, the terminal device further includes a state information acquisition unit that acquires state information of an electrical treatment device, which has been determined by the determination unit to be registered with the terminal device, from the electrical treatment device determined to be registered with the terminal device. The state information includes information indicating whether the registered electrical treatment device is in an in-treatment state or a treatment standby state in which the registered electrical treatment device is not in an in-treatment state. When the electrical treatment device is in the treatment standby state, the notification unit further provides notification to power OFF the electrical treatment device.

Preferably, the notification unit provides notification on hardware, which is provided on the unregistered electrical treatment device, to be used to perform a predetermined operation for the solution.

A treatment system according to another embodiment includes: at least one electrical treatment device; and a terminal device configured to wirelessly communicate with the at least one electrical treatment device. The terminal device includes:

an information storage unit that stores registration information for establishing a wireless communication connection with the at least one electrical treatment device;

a detection unit that detects a beacon signal emitted from the at least one electrical treatment device; and a determination unit that determines, on the basis of the registration information stored in the information storage unit and the beacon signal detected, whether the at least one electrical treatment device includes an unregistered electrical treatment device not registered with the terminal device. When the unregistered electrical treatment device is included, the determination unit further determines, on the basis of the beacon signal detected, whether the unregistered electrical treatment device comprises registration information of a device other than the terminal device. The terminal device further includes a notification unit that provides notification on information including a solution for an error, when the unregistered electrical treatment device includes the registration information of the device other than the terminal device.

According to yet another embodiment, a program is provided that is executed by a computer of a terminal device configured to wirelessly communicate with at least one electrical treatment device. The terminal device comprises a memory that stores registration information for establishing a wireless communication connection with the at least one electrical treatment device. The program causes the computer to execute: detecting a beacon signal emitted from the at least one electrical treatment device; determining, on the basis of the registration information stored in the memory and the beacon signal detected, whether the at least one electrical treatment device includes an unregistered electrical treatment device not registered with the terminal device; when the unregistered electrical treatment device is included, determining, on the basis of the beacon signal detected, whether the unregistered electrical treatment device includes registration information of a device other than the terminal device; and providing notification on information including a solution for an error, when the unregistered electrical treatment device includes the registration information of the device other than the terminal device.

Advantageous Effects of Invention

According to the present disclosure, security can be easily improved when using a wireless communication connection.

DESCRIPTION OF EMBODIMENTS

Embodiments of the present invention will be described below with reference to the drawings. In the following description, like components are given like numerals. Names and functions thereof are also the same. Thus, the detailed description of such components is not repeated.

System Configuration

Figure 1:
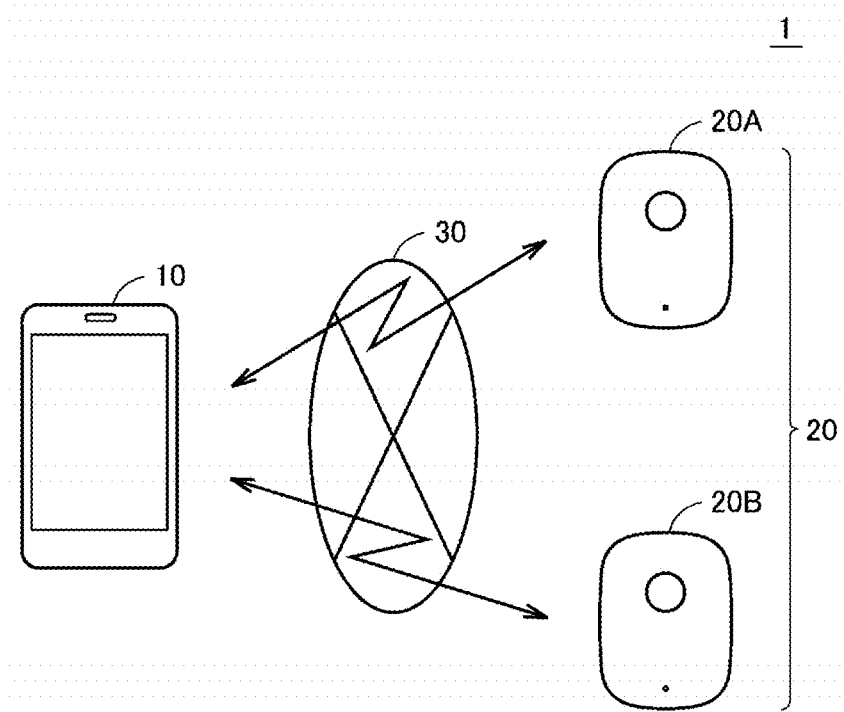
FIG. 1 is a diagram illustrating a schematic configuration of a treatment system.

FIG. 1 is a diagram illustrating a schematic configuration of a treatment system 1. Referring to FIG. 1, the treatment system 1 includes a terminal device 10, which is a user terminal, electrical treatment devices 20A, 20B, and a network 30. Hereinafter, when describing configurations and functions shared by the electrical treatment devices 20A, 20B, the electrical treatment devices 20A, 20B are collectively referred to as an "electrical treatment device 20".

The electrical treatment device 20 is a cordless type and includes a pad, a holder, and a main body portion that serve as a single unit when used. These portions are used in combination to provide treatment. The electrical treatment device 20 according to the present embodiment is a low-frequency treatment device that provides treatment such as easing user shoulder stiffness by supplying a low-frequency pulse. For example, the frequency of the low-frequency pulse current is from 1 Hz to 1200 Hz. However, the electrical treatment device 20 may be configured to use a pulse current of other frequency bands. In FIG. 1, only the main body portion of the electrical treatment device 20 is illustrated, and the pad and the holder are omitted from the diagram. The specific configuration of the electrical treatment device 20 will be described later.

The terminal device 10 is, for example, a smart phone including a touch panel. In the description hereinafter, a smartphone will be used as a representative example of the "terminal device". However, the terminal device may be a different terminal device such as a folding type mobile telephone, a tablet terminal device, a personal computer (PC), a personal data assistance (PDA), and the like.

The network 30 for connecting the terminal device 10 and the electrical treatment device 20 employs a short-range wireless communication system, typically BLUETOOTH low energy (BLE). As such, the terminal device 10 and the electrical treatment device 20 are BLE devices having a function of performing wireless communication using BLE, However, the network 30 is not limited thereto, and a different wireless communication system, such as BLUETOOTH or a wireless local area network (LAN), may be employed.

In the treatment system 1 according to the present embodiment, the terminal device 10 gives instructions to the electrical treatment devices 20A, 20B paired therewith via an application installed on the terminal device 10. The terminal device 10 displays various kinds of information on the display of the terminal device 10 and notifies the user of necessary information. Specific operations will be described in detail below.

Configuration of Electrical Treatment Device 20

Figure 2:
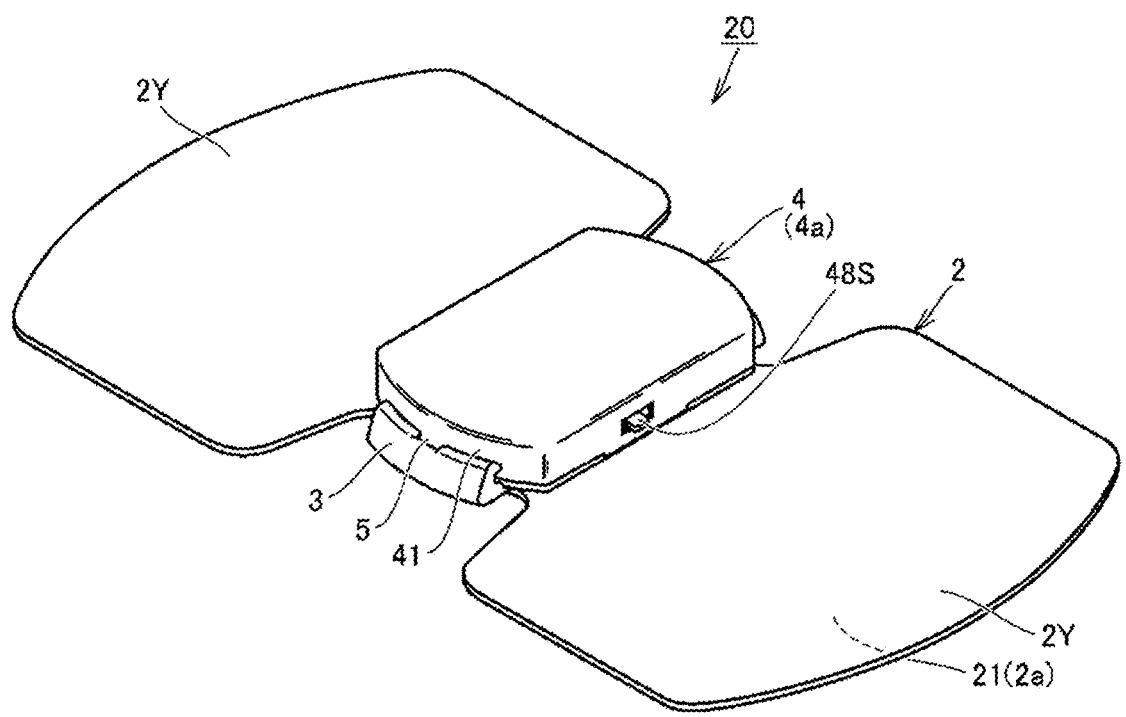
FIG. 2 is a perspective view illustrating a configuration of an electrical treatment device.
Figure 3:
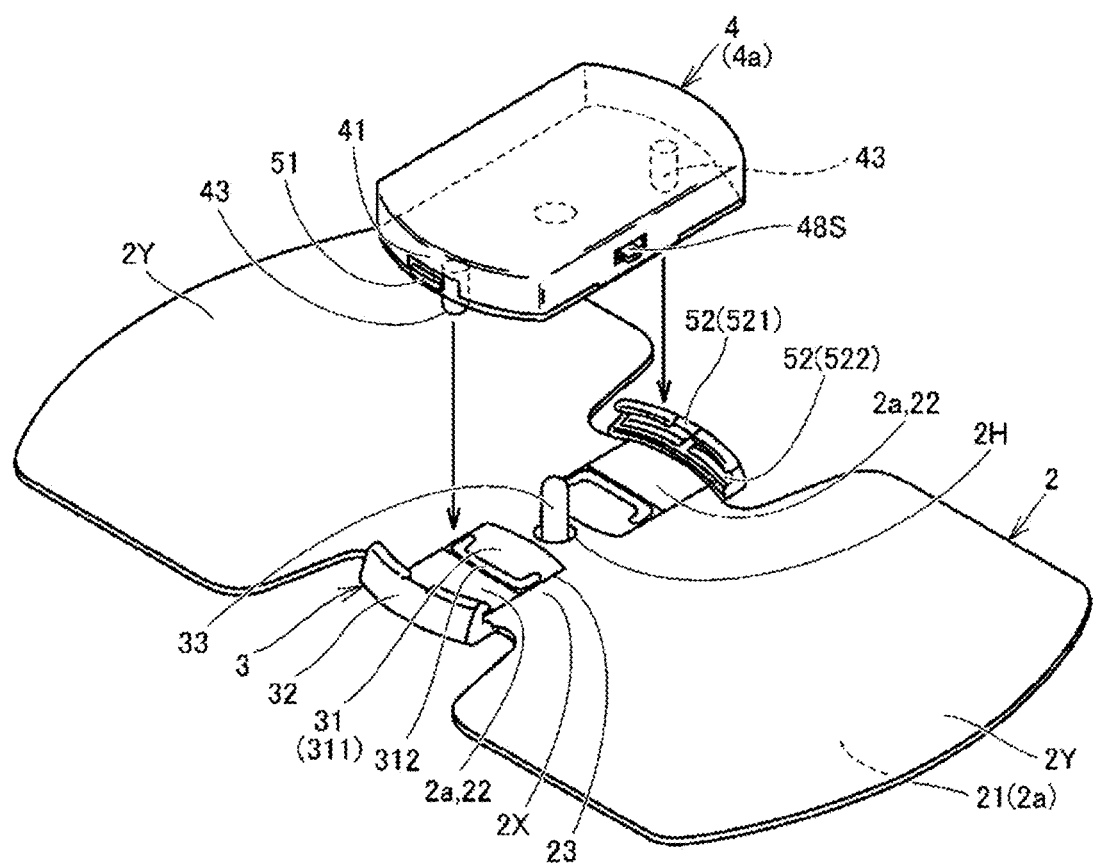
FIG. 3 is a perspective view illustrating a main body portion, a holder, and a pad of the electrical treatment device in a state where the main body portion is separated from the holder and the pad.

FIG. 2 is a perspective view illustrating the configuration of the electrical treatment device 20. FIG. 3 is a perspective view illustrating a main body portion 4, a holder 3, and a pad 2 of the electrical treatment device 20 in a state where the main body portion 4 is separated from the holder 3 and the pad 2.

Referring to FIGS. 2 and 3, the electrical treatment device 20 is a so-called cordless type low-frequency treatment device and includes the pad 2, the holder 3, and the main body portion 4.

The pad 2 has a sheet-like shape and is configured to attach to the user's body. A conductive layer 2a is provided on a body-side portion 21 surface (lower surface), of the outer surfaces of the pad 2, that faces the body. The pad 2 is attached to the user's skin by using a conductive gel or the like, and a low-frequency pulse is supplied to the user through the conductive layer 2a.

Referring to FIG. 3, the pad 2 includes an attachment portion 2X and a treatment portion 2Y. The attachment portion 2X is held by the holder 3. A window portion 23 and a through hole 2H are provided at the attachment portion 2X. A positioning protrusion 312 of the holder 3 is disposed on the inside of the window portion 23. An interlock pin 33 of the holder 3 is inserted through the through hole 2H. The treatment portion 2Y is provided on both the left and right sides of the attachment portion 2X, and the conductive layer 2a is exposed on the body-side portion 21 of the treatment portion 2Y.

The conductive layer 2a is also exposed on the surface facing the main body portion 4 at the attachment portion 2X, and the exposed portion constitutes a pad side electrode portion 22. The pad side electrode portion 22 is formed to establish an electrical connection with a main body portion side electrode portion 43, and a conductive layer 2a corresponding to one electrode portion (for example, a positive electrode) is exposed at one end of the attachment portion 2X, and a conductive layer 2a corresponding to another electrode portion (for example, a negative electrode) is exposed at the other end of the attachment portion 2X.

Referring to FIG. 3, the holder 3 includes a pad holding portion 31 with a plate-like shape and a pair of wall portions 32 erected from both ends of the pad holding portion 31. An attachment portion 2X of the pad 2 is disposed on an upper surface 311 of the pad holding portion 31. Double-sided adhesive tape, glue, adhesive, or the like is disposed, as necessary, between the upper surface 311 and the attachment portion 2X.

The positioning protrusion 312 is provided on the pad holding portion 31. By fitting the inner peripheral edge of the window portion 23 provided in the pad 2 to the positioning protrusion 312, the pad 2 can be positioned with respect to the holder 3. The interlock pin 33 is centrally disposed on the pad holding portion 31. When attaching the pad 2 to the holder 3, the interlock pin 33 is inserted into the through hole 2H.

The pad 2 is a consumable item, and the pad 2 can be detachably attached to the main body portion 4, thus allowing replacement of the pad 2. In the present embodiment, the holder 3 holds the pad 2 such that the holder 3 and the pad 2 are integrated, and the main body portion 4 is configured to be detachably attached to the pad 2 and the holder 3. The pad 2 can be replaced together with the holder 3, or it is also possible to reuse the holder 3 as necessary.

Referring to FIGS. 2 and 3, the main body portion 4 includes as an outer cover a case 4a with a substantially rectangular parallelepiped shape. A guiding/engagement portion 5 (FIG. 2) is formed between the case 4a and the holder 3, and the main body portion 4 (case 4a) is detachably attached to the holder 3. The guiding/engagement portion 5 includes a protrusion 51 (FIG. 3) formed on a side surface 41 of the case 4a and a groove portion 52 (FIG. 3) formed in each of the wall portions 32 of the holder 3.

Referring to FIG. 3, the groove portion 52 includes a vertical groove portion 521 and a lateral groove portion 522. The vertical groove portion 521 is formed in the vertical direction and opens upward. The lateral groove portion 522 is formed in the lateral direction and opens at both ends. When the main body portion 4 is attached to the holder 3, both of the protrusion 51 and the groove portion 52 move closer together in a facing direction and engage together. By rotating and moving the main body portion 4 with respect to the holder 3, the engagement between the two is released, and the main body portion 4 can be removed from the holder 3.

With the main body portion 4 attached to the holder 3, the main body portion 4 supplies a low-frequency pulse current to the conductive layer 2a of the pad 2. Specifically, the main body portion 4 includes a pair of the main body portion side electrode portions 43, a substrate (not illustrated), an electric circuit (not illustrated), and an interlock mechanism (not illustrated). The electric circuit includes various control devices and is mounted on the surface of the substrate.

Examples of the control devices include a processor for performing various processes, a memory for storing programs, data, and the like, a communication interface for wirelessly communicating various types of data with the terminal device 10, and a waveform generation output circuit for boosting the power source voltage and generating and outputting a low-frequency pulse current (treatment current), and the like.

The substrate, the electric circuit, and the interlock mechanism are provided inside the main body portion 4

(case 4a). A power source (not illustrated) such as a battery is also provided inside the main body portion 4 (case 4a). A display portion (not illustrated) such as a switch 48S (FIG. 2), light emitting diode (LED), and a button (not illustrated) are provided on the outside of the case 4a.

In a state in which the main body portion 4 is attached to the holder 3, an end portion of the main body portion side electrode portion 43 abuts the pad side electrode portion 22. Thus, the main body portion side electrode portion 43 and the pad side electrode portion 22 are electrically connected, whereby the electric circuit can supply a low-frequency pulse current to the pad side electrode portion 22.

Configuration of Terminal Device 10

Figure 4:
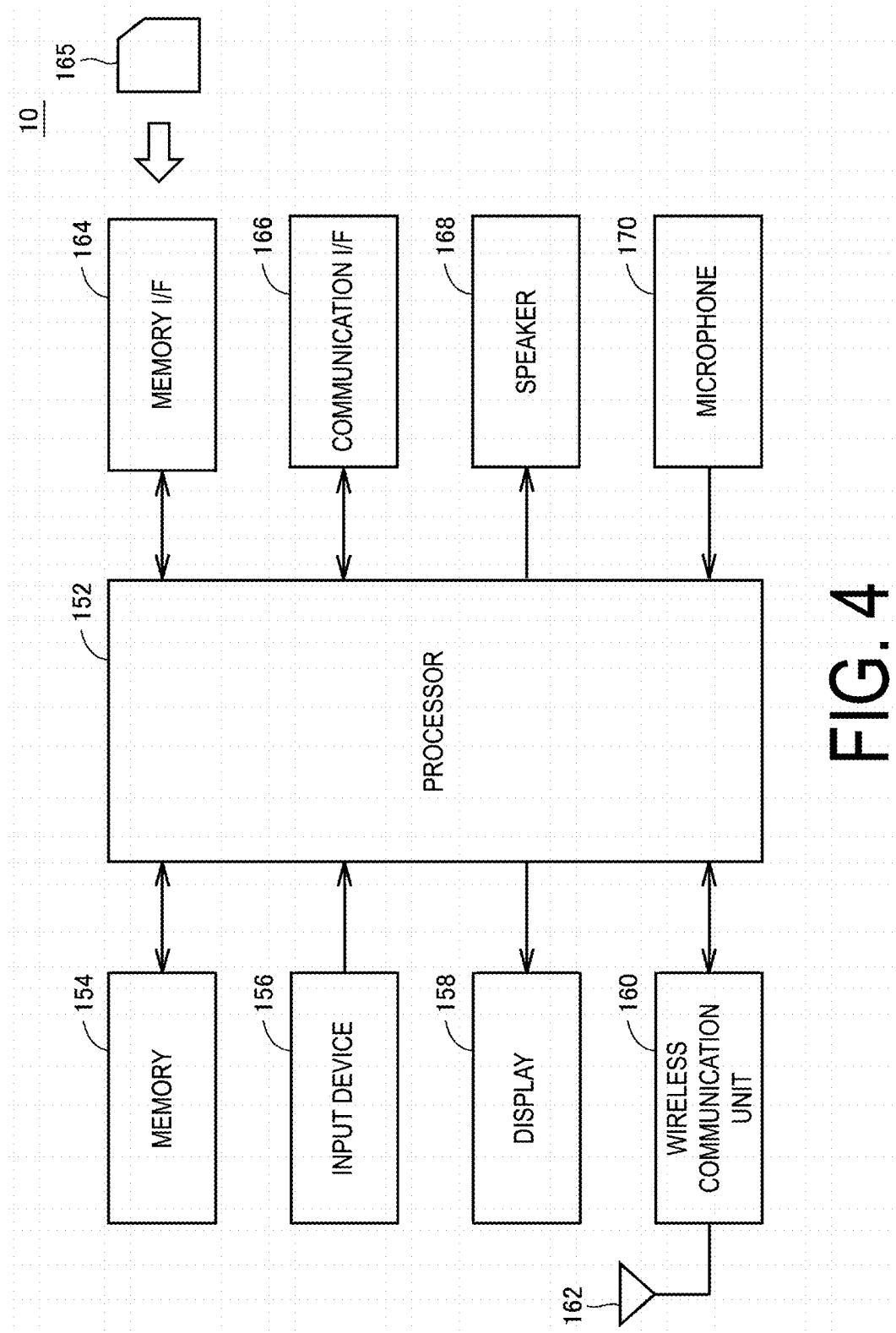
FIG. 4 is a block diagram illustrating an example of a hardware configuration of a terminal device.

FIG. 4 is a block diagram illustrating an example of a hardware configuration of the terminal device 10. Referring to FIG. 4, the terminal device 10 includes, as main components, a processor 152, a memory 154, an input device 156, a display 158, a wireless communication unit 160, a memory interface (I/F) 164, a communication interface (I/F) 166, a speaker 168, and a microphone 170.

The processor 152 typically may be an arithmetic processing unit such as a central processing unit (CPU) or a multi processing unit (MPU). The processor 152 functions as a control unit that controls the operation of components of the terminal device 10 by reading out and executing a program stored in the memory 154. By executing the program, the processor 152 executes processing (steps) of the terminal device 10 described later.

The memory 154 is realized by random access memory (RAM), read-only memory (ROM), flash memory, and the like. Programs executed by the processor 152, data used by the processor 152, and the like are stored in the memory 154.

The input device 156 receives an operation input to the terminal device 10. Typically, the input device 156 is realized by a touch panel. The touch panel is provided on the display 158 that functions as a display portion, and is, for example, an electrostatic capacitive type. The touch panel detects touch operations on the touch panel by an external object at predetermined intervals of time and inputs touch coordinates to the processor 152. However, the input device 156 may be a button or the like.

The wireless communication unit 160 connects to a mobile communication network via a communication antenna 162 and transmits and receives signals for wireless communication. Accordingly, the terminal device 10 can communicate with other communication devices via a mobile communication network such as long term evolution (LTE), for example.

The memory interface 164 reads data from an external storage medium 165. The processor 152 reads the data stored in the storage medium 165 via the memory interface 164 and stores the data in the memory 154. The processor 152 reads the data from the memory 154 and stores the data in the external storage medium 165 via the memory interface 164.

The storage medium 165 may also be a compact disc (CD), digital versatile disk (DVD), BLU-RAY disc (BL)), universal serial bus (USB) memory, secure digital (SIS) memory card, and the like that store programs in a nonvolatile manner.

The communication interface (I/F) 166 is a communication interface for exchanging various data between the terminal device 10 and the electrical treatment device 20 and is realized by an adapter, a connector, or the like. As the communication method, for example, a wireless communication method such as BLUETOOTH low energy (BLE), wireless LAN, and the like may be employed.

The speaker 168 converts an audio signal from the processor 152 to voice and outputs the same to the outside of the terminal device 10. The microphone 170 receives an audio input for the terminal device 10 and provides to the processor 152 an audio signal corresponding to the audio input.

System Operation Summary

An operation overview of the treatment system 1 will be described with reference to FIGS. 5 to 14. Note that the screens illustrated in FIGS. 5 to 14 are screens displayed on the display 158 after activating an application for electrical treatment installed on the terminal device 10 (hereinafter, also simply referred to as a "treatment app").

Device Connection

Figure 5:
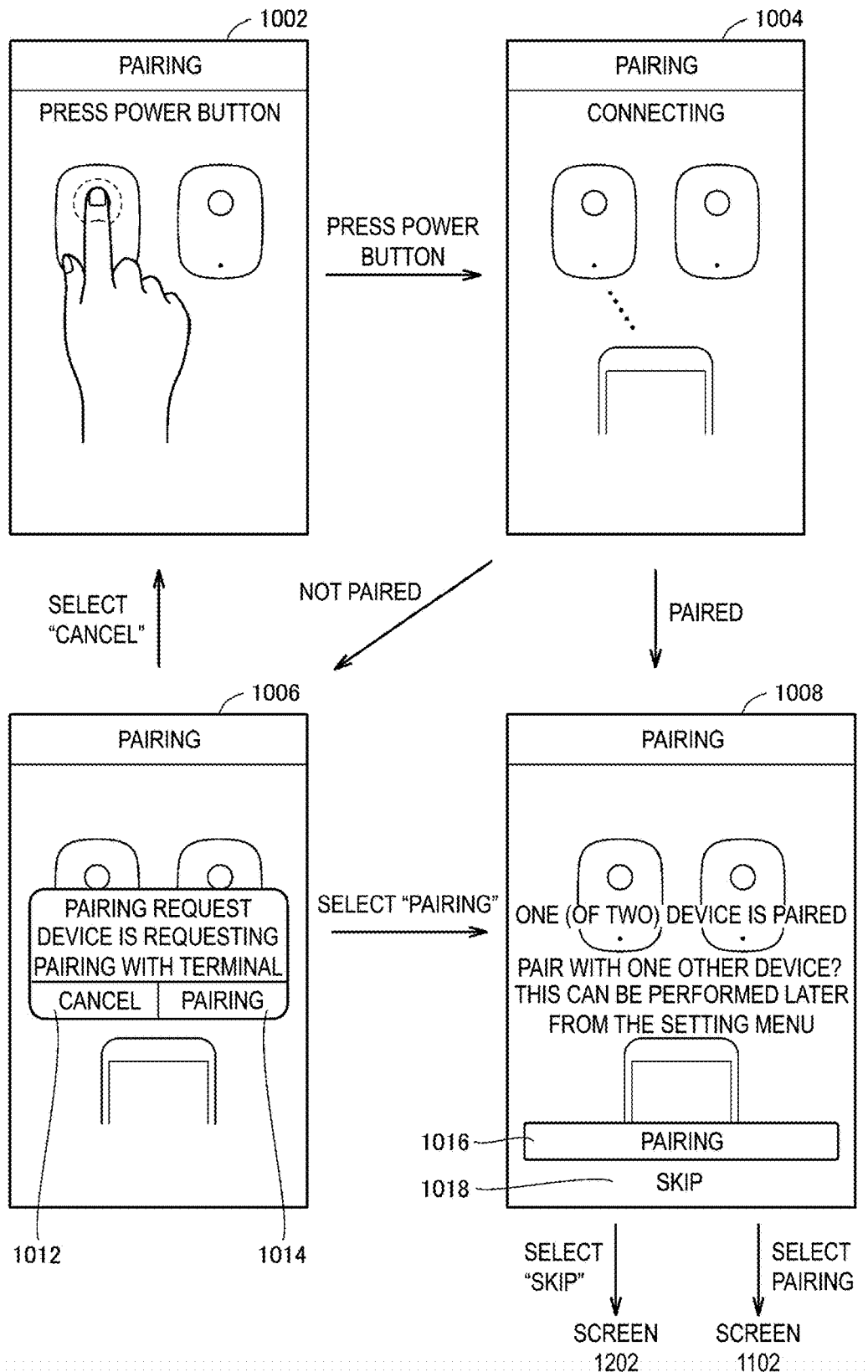
FIG. 5 is a screen transition diagram for explaining a flow of connecting together the terminal device and the electrical treatment device.
Figure 6:
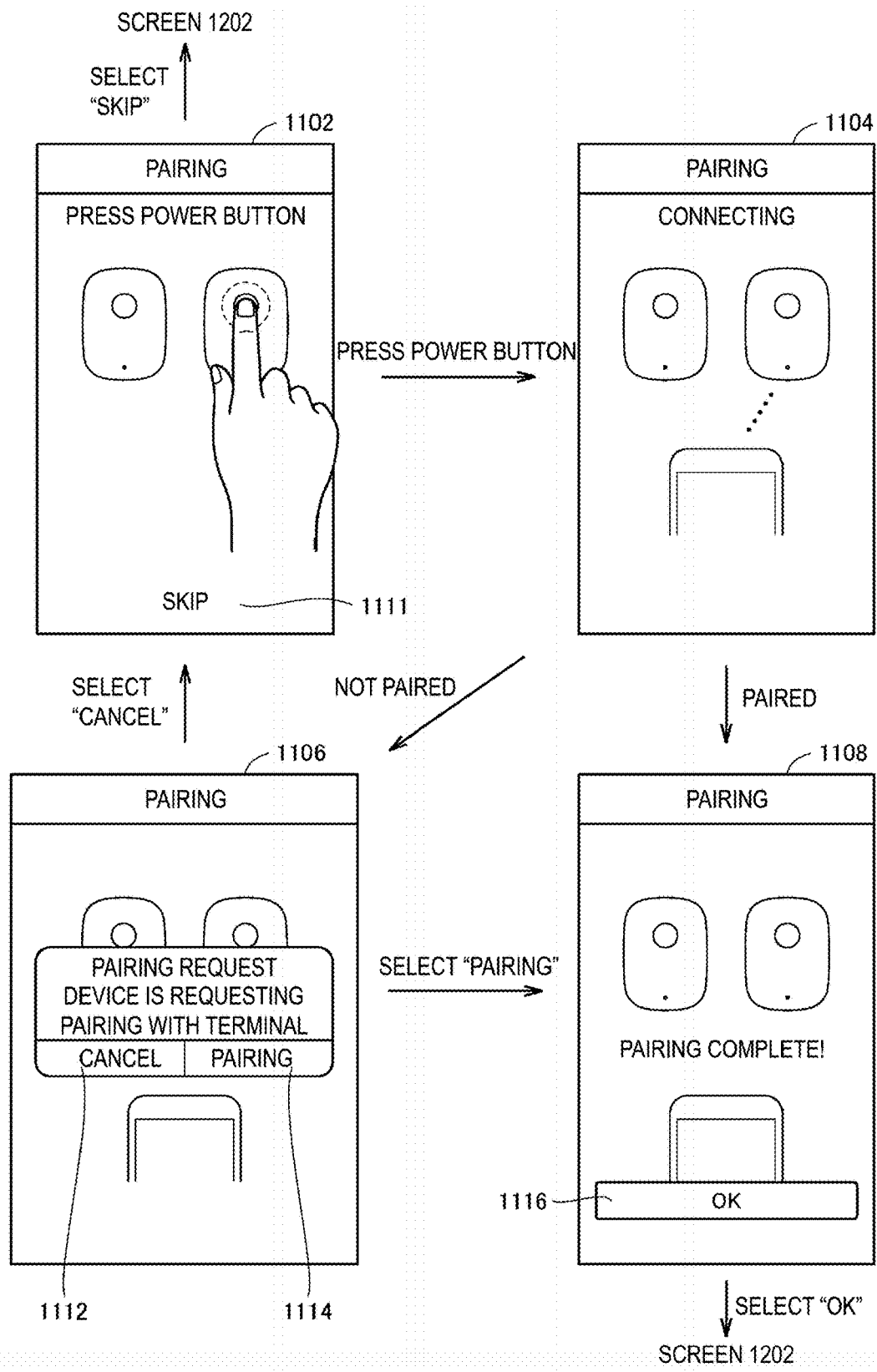
FIG. 6 is a screen transition diagram for explaining a flow of connecting together the terminal device and the electrical treatment device.

First, the flow when the terminal device 10 is connected to the electrical treatment devices 20A, 20B will be described. FIGS. 5 and 6 are screen transition diagrams for explaining the flow of connecting together the terminal device 10 and the electrical treatment device 20.

The flow until the connection between the terminal device 10 and the first electrical treatment device 20 (for example, the electrical treatment device 20A) is completed will be described with reference with FIG. 5. When the terminal device 10 receives an instruction to activate the treatment app via the input device 156, the terminal device 10 displays a screen 1002 after a splash screen. Note that the terminal device 10 may display a guidance screen for schematically describing the contents of the treatment app after the splash screen. The screen 1002 is a screen that prompts for the power source of the electrical treatment device 20, which is paired with the terminal device 10, to be turned ON by displaying words such as "Press the power button" or an animation in which a finger presses down the power button of the electrical treatment device 20.

The terminal device 10 that performs wireless communication according to the BLE method starts a scanning operation, after the treatment app is activated, in order to receive (detect) a beacon signal, called an advertisement packet (hereinafter, also referred to simply as "advertisement") emitted from the electrical treatment device 20, which is the terminal on the sending side. The scan operation is an operation of detecting an advertisement including a device ID that satisfies a predetermined condition and is performed for a predetermined amount of time (for example, 180 seconds).

The advertisement is used to inform surrounding devices of the presence of the treatment device and that the treatment device is waiting to connect to a surrounding device. The advertisement includes information such as a device ID that uniquely identifies the treatment device, the type of service the terminal provides, operation mode of the treatment device, the communication protocol version, and the like.

The device ID includes type information (for example, information indicating that the device type is an "electrical treatment device"), classification information (for example, information indicating a sale area of the device and the model of the device), unique information (for example, a unique code assigned to the device), and the like. In the present embodiment, the terminal device 10 detects, via the scanning operation, an advertisement including the device ID having type information indicating "electrical treatment device".

Next, when the power source of the electrical treatment device 20 is pressed down by the user in accordance with the screen 1002, the terminal device 10 displays a screen 1004 and begins a connection process with the electrical treatment device 20. Specifically, when detecting, via the scanning operation, an advertisement including an operation mode "pairing request mode" for requesting pairing and a device type "electrical treatment device", the terminal device 10 determines that the electrical treatment device 20 emitting the advertisement is not paired (no pairing information is registered). Pairing information is information required to establish a wireless communication connection between the terminal device 10 and the electrical treatment device 20 and includes, for example, the device ID for pairing, MAC address, service information, and the like. In this case, the terminal device 10 displays a screen 1006 that prompts for confirmation of the pairing request.

The screen 1006 includes a cancel button 1012 for canceling the pairing request and a pairing button 1014 for accepting the pairing request. When the terminal device 10 receives selection of the cancel button 1012 at the screen 1006, the terminal device 10 displays the screen 1002. When the terminal device 10 receives selection of the pairing button 1014, the terminal device 10 displays a screen 1008.

When detecting, via the scanning operation, an advertisement including an operation mode "connection request mode" for requesting wireless communication connection and a device type "electrical treatment device" at the screen 1004 and also when pairing information included in the advertisement has been registered in the terminal device 10, the terminal device 10 determines that the electrical treatment device 20 emitting the advertisement is paired therewith, and displays the screen 1008.

The screen 1008 is a screen showing that pairing between the terminal device 10 and one unit of the electrical treatment device 20 (for example, the electrical treatment device 20A) has been completed and a wireless connection therebetween has been established. When the pairing between the terminal device 10 and the electrical treatment device 20A is the first time the two devices have been paired, the terminal device 10 stores pairing information such as the device ID of the electrical treatment device 20A in the memory 154. The electrical treatment device 20A receives the device ID and the like of the terminal device 10 from the terminal device 10 and stores the same in an internal memory thereof as pairing information.

Note that in a case in which the electrical treatment device 20A has not stored pairing information in the internal memory thereof, the electrical treatment device 20A automatically emits an advertisement including a "pairing request mode", by the user simply pressing the power button of the electrical treatment device 20A a single time (a brief press operation (for example, less than 1 second)). Thus, the user does not need to perform a long press operation (for example, a pressing operation of one second or more), and the electrical treatment device 20A and the terminal device 10 can easily be paired.

The screen 1008 includes a pairing button 1016 for performing pairing with another electrical treatment device 20 (for example, the electrical treatment device 20B) and a skip button 1018 for not performing pairing. When receiving selection of the pairing button 1016, the terminal device 10 displays a screen 1102 (see FIG. 6). When receiving selection of the skip button 1018, the terminal device 10 displays a screen 1202 (see FIG. 7, described later) relating to setting the treatment content to be performed by the electrical treatment device 20. In a case where the user wants to connect together only the terminal device 10 and the electrical treatment device 20A or perform the connection between the terminal device 10 and the electrical treatment device 20B at a later time, the user can skip the flow of connecting together the terminal device 10 and the electrical treatment device 20B by selecting the skip button 1018.

Here, the electrical treatment device 20 according to the present embodiment is configured such that the pairing information of only one BLE device can be stored in a memory thereof. In a case where the electrical treatment device 20 stores pairing information of any of BLE devices in a memory thereof, the electrical treatment device 20 operates in connection request mode and emits an advertisement for requesting self-authentication to establish a wireless communication connection. In a case where the electrical treatment device 20 does not store any of BLE devices in a memory thereof, the electrical treatment device 20 operates in pairing request mode and emits an advertisement for requesting pairing. In other words, the electrical treatment device 20 does not operate in pairing request mode when pairing information is stored.

Thus, when the terminal device 10 has detected an advertisement including a pairing request mode, the terminal device 10 determines that the electrical treatment device 20 emitting the advertisement has not been paired. When the terminal device 10 has detected an advertisement including a connection request mode, the terminal device 10 determines that the electrical treatment device 20 emitting the advertisement has been paired with a BLE device.

Next, the flow until the connection between the terminal device 10 and the second electrical treatment device 20 (in this example, the electrical treatment device 20B) is completed will be described with reference with FIG. 6. Receiving selection of the pairing button 1016 at the screen 1008 (see FIG. 5), the terminal device 10 displays the screen 1102. The screen 1102 is a screen that prompts for the power source of the second electrical treatment device 20B, which is to be paired with the terminal device 10, to be turned ON. Note that, receiving selection of a skip button 1111, the terminal device 10 displays the screen 1202 (see FIG. 7, described below).

Next, when the power source of the electrical treatment device 20B is pressed down by the user in accordance with the screen 1102, the terminal device 10 displays a screen 1104 and begins the connection process with the electrical treatment device 20B. When the terminal device 10 determines, via a scanning operation, that the electrical treatment device 20B has not been paired, the terminal device 10 displays a screen 1106 that prompts for confirmation of the pairing request.

The screen 1106 includes a cancel button 1112 for the pairing request and a pairing button 1114 for accepting the pairing request. When the terminal device 10 receives selection of the cancel button 1112 at the screen 1106, the terminal device 10 displays the screen 1102. When the terminal device 10 receives selection of the pairing button 1114, the terminal device 10 displays a screen 1108.

When the terminal device 10 determines, via a scanning operation, that the electrical treatment device 20B has been paired with the terminal device 10 at the screen 1104, the terminal device 10 displays the screen 1108.

The screen 1108 is a screen showing that pairing between the terminal device 10 and the electrical treatment devices 20A, 20B has been completed and a wireless connection has been established between the devices. When the terminal device 10 receives selection of an OK button 1116, the terminal device 10 displays the screen 1202 (see FIG. 7, described below).

Setting of Treatment Content

Figure 7:
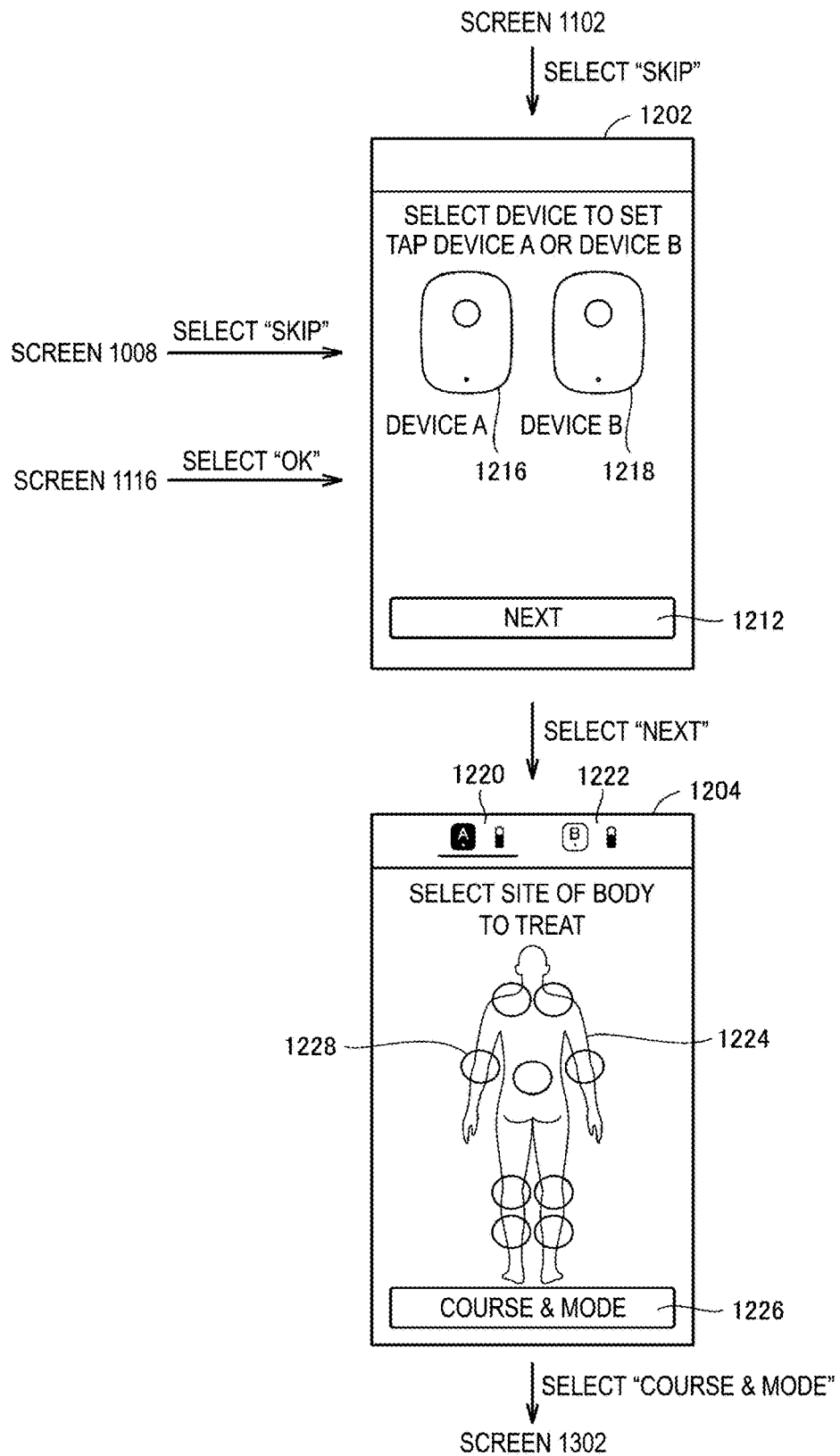
FIG. 7 is a screen transition diagram for explaining a flow of setting the treatment content via the terminal device.
Figure 8:
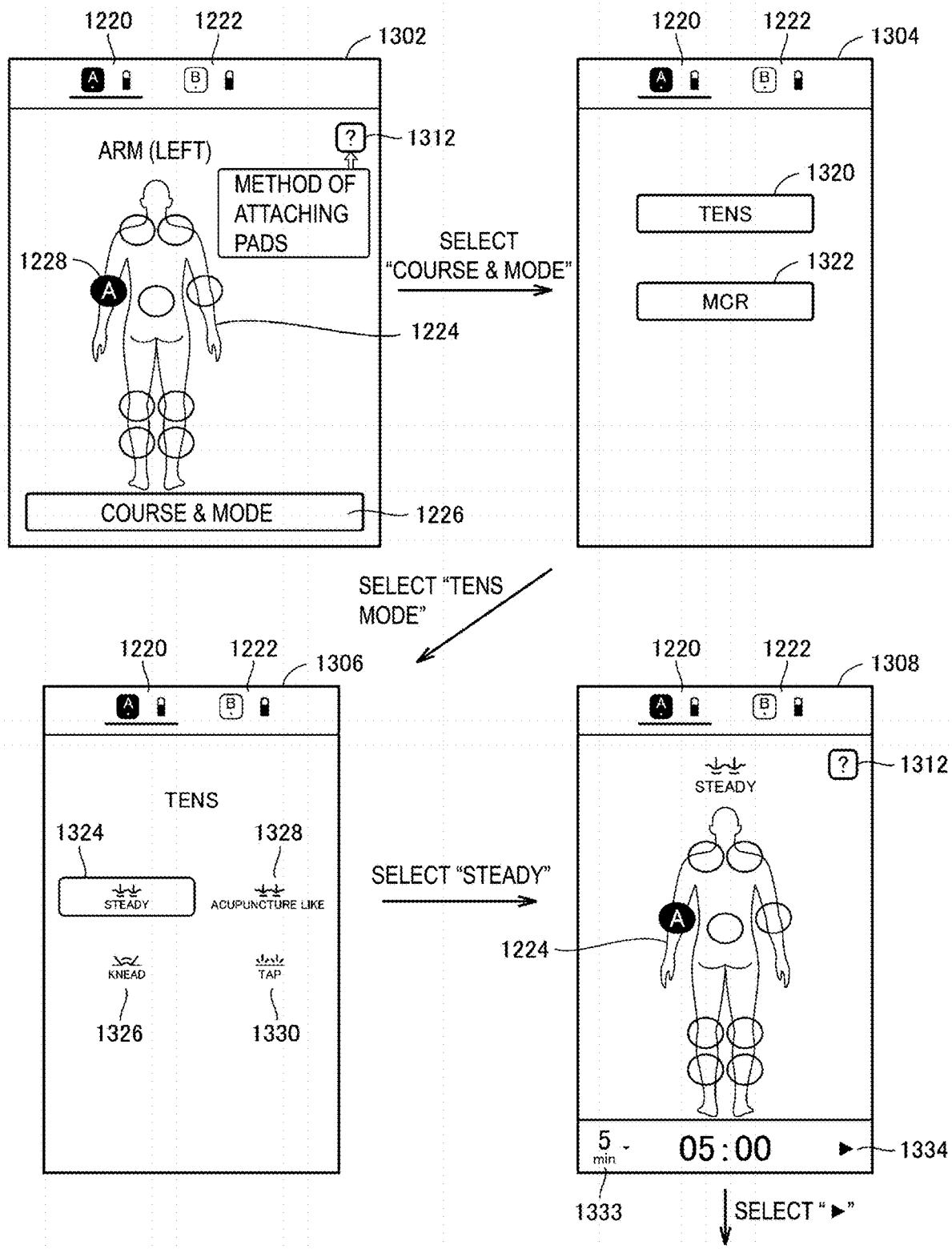
FIG. 8 is a screen transition diagram for explaining a flow of setting the treatment content via the terminal device.

Next, the flow in which the terminal device 10 sets the treatment content that is performed by the electrical treatment device 20 will be described. FIGS. 7 and 8 are screen transition diagrams for explaining the flow of setting the treatment content via the terminal device 10.

Referring to FIG. 7, the terminal device 10 displays the screen 1202 upon receiving selection of the skip button 1018 on the screen 1008 (see FIG. 5), selection of the skip button 1111 on screen 1102 (see FIG. 6), or selection of the OK button 1116 on screen 1108 (see FIG. 6).

The screen 1202 is a screen for selecting whether to set a treatment content Ta performed by the electrical treatment device 20A or a treatment content Tb performed by the electrical treatment device 20B. The terminal device 10 associates the first electrical treatment device 20A, to which connection was first established, with a device A on the treatment app screen and associates the second electrical treatment device 20B, to which connection was established subsequently, with a device B on the treatment app screen. The treatment app has a state in which the device A is recognized as the electrical treatment device 20A and the device B is recognized as the electrical treatment device 20B. In screen 1202, the device A corresponds to a device object 1216 and the device B corresponds to a device object 1218.

Here, the user knows that the electrical treatment device connected first is associated with the device A on the treatment app screen and the electrical treatment device connected second is associated with the device B on the treatment app screen. Note that the "device A" and "device B" may be displayed as "first device" and "second device", for example, on the treatment app screen.

Receiving selection (a tap) of the device object 1216 from the user, the terminal device 10 highlights the device object 1216 to notify the user of the selection (for example, the device object 1216 flashes, or the like). In addition, in order to notify the user that the device A (the device object 1216) is associated with the electrical treatment device 20A, the terminal device 10 transmits a control signal to the electrical treatment device 20A to flash an LED. The electrical treatment device 20A flashes an LED in accordance with the received control signal.

This allows the user to know that the device A (the device object 1216) that the user selected on the treatment app corresponds to the electrical treatment device 20A, that is, the selected device actually. Receiving selection of a button 1212 by which the device object 1216 was selected, the terminal device 10 begins the flow of setting the treatment content Ta.

Receiving selection of the device object 1218 from the user, the terminal device 10, via operation similar to that described above, highlights the device object 1218 and causes the LED of the electrical treatment device 20B to flash. Next, receiving selection of the button 1212, the terminal device 10 begins the flow of setting the treatment content Tb.

However, in a case in which the screen 1202 has transitioned from the screen 1008 (see FIG. 5) or the screen 1102, the connection between the terminal device 10 and the electrical treatment device 20B is not established. Thus, the terminal device 10 disables selection of the device object 1218 and does not accept the selection.

In the following description, the user selects the button 1212 after selecting the device object 1216 corresponding to the device A on the treatment app screen. In this case, the terminal device 10 displays a screen 1204 for beginning the flow of setting the treatment content Ta corresponding to the electrical treatment device 20A.

The screen 1204 is a screen for selecting a portion of the body that treatment is desired for (for example, shoulder, arm, waist, knee, calf, and the like). Specifically, the screen 1204 includes a tab 1220 corresponding to the device A on the treatment app screen, a tab 1222 corresponding to the device B on a treatment app screen, a body object 1224, and a button 1226 for transitioning to a course and mode setting screen.

In the screen 1204, the tab 1220 corresponding to the device A is highlighted because the treatment content Ta is currently being set. Note that when one of the treatment contents (in this example, the treatment content Ta) is being set, selection of the tab 1222 corresponding to the device B is disabled, and the other treatment content (in this example, the treatment content Tb) cannot be set. Specifically, the treatment content Tb cannot be set until the treatment content Ta has been confirmed and transition to a waiting-to-start-treatment screen (a screen 1308 in FIG. 8) has been completed. This is to prevent the user from being confused about with which device treatment content that is currently being set is associated. When the terminal device 10 receives selection of a left arm portion 1228 of the body object 1224 from the user, the terminal device 10 displays a screen 1302 illustrated in FIG. 8.

Referring to FIG. 8, on the screen 1302, "A" is displayed on the left arm portion 1228, and information "arm (left)" indicating that this portion is the left arm is displayed. In this way, the terminal device 10 notifies the user that, next, the setting of the treatment content for the left arm begins. Typically, because the user knows from the previous screen 1202 (see FIG. 7) that the device A on the treatment app screen corresponds to the electrical treatment device 20A, the user attaches the electrical treatment device 20A to the left arm. In addition, receiving selection of a help button 1312 from the user, the terminal device 10 displays a guide screen (not illustrated) for a method of attaching the main body portion 4 to the pad 2 and the holder 3 and a guide screen (not illustrated) for a method of attaching the pad 2 to the selected site (in this example, the left arm). Receiving selection of the button 1226 from the user, the terminal device 10 displays a screen 1304.

A button 1320 for selecting a transcutaneous electrical nerve stimulation (TENS) course and a button 1322 for selecting a microcurrent (MCR) course are displayed on the screen 1304. The TENS course is a course that provides electrical stimulation to sensory nerves to suppress and reduce pain. The MCR course is a course that runs microcurrents into the body to stimulate muscles and repair cells. In a case where the user selects the TENS course and when the terminal device 10 receives selection of the button 1320, the terminal device 10 displays a screen 1306.

The screen 1306 is a mode selection screen for the TENS course. Specifically, buttons 1324, 1326, 1328, 1330 for selecting modes "steady", "knead", "acupuncture like", and "tap" are displayed on the screen 1306. Here, in a case where the user selects the mode "steady" and when the terminal device 10 receives selection of the button 1324, the terminal device 10 displays the screen 1308.

The screen 1308 is a screen in a state of completion of the setting of the treatment content Ta and waiting for the start of treatment. Specifically, a tab 1333 for setting a treatment time and a start button 1334 for starting treatment are displayed on the screen 1308. The user may set a treatment time (for example, 5 minutes) by selecting the tab 1333. Note that on the screen 1308, because the setting of the treatment content Ta is complete, the tab 1222 can be selected allowing the treatment content Tb to be set. The procedure for setting the treatment content Tb is same as the procedure for the treatment content Ta described above.

When the terminal device 10 receives selection of the start button 1334 from the user, the terminal device 10 instructs the electrical treatment device 20A to start treatment in accordance with the set treatment content Ta and displays an in-treatment screen (a screen 1402 in FIG. 9, described later).

However, the terminal device 10 is configured such that, in a case where the terminal device 10 determines that the pad 2 is not attached to the user on the basis of information received from the electrical treatment device 20A, the terminal device 10 disables selection of the start button 1334 and does not receive a treatment start instruction.

Specifically, the electrical treatment device 20 has a function of detecting whether the pad 2 is in a state of being attached (affixed) to the user or a state of being not attached (peeled off) to the user. Detection of the state of attachment of the pad 2 is performed by applying a weak current to the pad 2 at a level that does not stimulate the user's body. The electrical treatment device 20 determines that the pad 2 is attached to the user if a weak current is detected. The electrical treatment device 20 determines that the pad 2 is not attached to the user if no weak current is detected. The electrical treatment device 20 periodically transmits to the terminal device 10 information indicating the state of attachment of the pad 2 to the user. Thus, the terminal device 10 can constantly ascertain the state of attachment of the pad 2 to the user. This can prevent a treatment start instruction when the pad 2 is not attached to the user.

Operation During Treatment

Next, the flow during treatment by the electrical treatment device 20 will be described. FIG. 9 is a screen transition diagram for explaining the flow of operation with the terminal device 10 during treatment.

Figure 9:
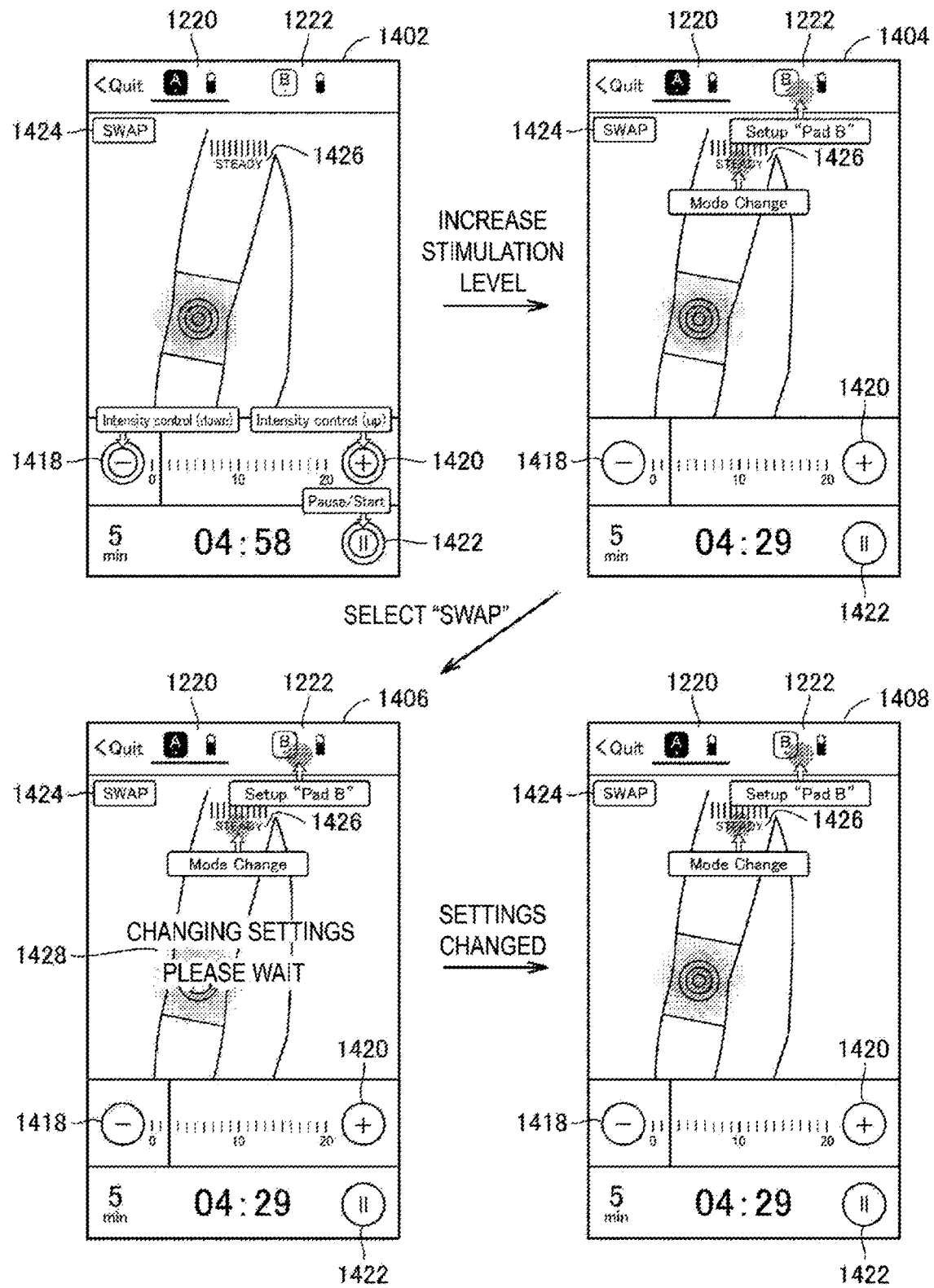
FIG. 9 is a screen transition diagram for explaining a flow of operation with the terminal device during treatment.

Referring to FIG. 9, a button 1418 for lowering a stimulation level, a button 1420 for increasing the stimulation level, a button 1422 for starting and stopping treatment, and a SWAP button 1424 for changing the treatment content are displayed on the screen 1402. In addition, the screen 1402 shows a site receiving treatment, by the electrical treatment device 20A corresponding to the device A on the treatment app screen, on the left arm in accordance with the treatment content Ta. The user can implement transition to the screen 1306 (see FIG. 8) by selecting a button 1426 and set the mode again. The user can also select the buttons 1418, 1420 to change the stimulation level. In the illustrated screen 1402, the stimulation level is set to "1".

Here, a case is assumed where the user, after time has elapsed since the scene of the screen 1402, feels that the current stimulation level is weak and selects the button 1420 to increase the stimulation level. In a screen 1404 after a predetermined amount of time has elapsed since the scene of the screen 1402, the stimulation level is set to "2". In addition, in a case where the terminal device 10 is operated to raise the stimulation level by the user, the terminal device 10 instructs the electrical treatment device 20A corresponding to the device A to raise the stimulation level. The electrical treatment device 20A increases the stimulation level (increases current) in accordance with the instruction.

In this example, the treatment content Ta is set as follows: selected site: left arm, course: TENS, mode: steady, time: 5 minutes. The treatment content Tb is set as follows: selected site: waist, course: MCR, mode: microcurrent, time: 1 hour. The user, having perceived that the electrical treatment device 20A is attached to the "left arm" of the user and the electrical treatment device 20B is attached to the "waist" of the user, sets the treatment content as described above.

However, take, for example, a case where actually the electrical treatment device 20A is attached to the "waist" and the electrical treatment device 20B is attached to the "left arm". In this case, the treatment content Ta performed by the electrical treatment device 20A is performed on the "waist" of the user rather than on the "left arm" of the user, and the treatment content Tb performed by the electrical treatment device 20B is performed on the "left arm" of the user rather than the "waist" of the user. Specifically, the electrical treatment device 20A increases the stimulation level in accordance with an instruction from the terminal device 10, but the increase in the stimulation level will be reflected at the "waist" of the user rather than at the "left arm" of the user. This makes the user realize that attachment of the electrical treatment device 20A and attachment of the electrical treatment device 20B are the other way around, differently from how the user perceived.

In such cases, the user can reattach the electrical treatment device 20A to the "left arm" and the electrical treatment device 20B to the "waist" to receive the desired treatment set by the user. However, peeling off each of the pads 2 of the electrical treatment devices 20A, 20B and reattaching these pads to the correct locations is cumbersome. To avoid this, the terminal device 10 has a SWAP function whereby the treatment content corresponding to the electrical treatment device 20A and the treatment content corresponding to the electrical treatment device 20B can be swapped.

Specifically, receiving selection of the SWAP button 1424, the terminal device 10 displays a screen 1406. Here, information 1428 indicating that the setting change is being implemented is displayed on the screen 1406.

Specifically, the terminal device 10 instructs the electrical treatment devices 20A, 20B to cease treatment. Next, the terminal device 10 changes the association so that the electrical treatment devices 20A, 20B, i.e., the actual devices, are associated with the devices B, A on the treatment app screen, respectively. Also, the terminal device 10 changes the treatment content Ta performed by the electrical treatment device 20A to the treatment content Tb set for the waist and changes the treatment content Tb performed by the electrical treatment device 20B to the treatment content Ta set for the left arm.

Thus, when the SWAP button 1424 is selected, the device B on the treatment app screen is associated with the electrical treatment device 20A attached to the "waist", and the treatment content Ta performed by the electrical treatment device 20A is set to: selected site: waist, course: MCR, mode: microcurrent, time: 1 hour. Also, the electrical treatment device 20B attached to the "left arm" is associated with the device A on the treatment app screen, and the treatment content Tb performed by the electrical treatment device 20B is set to: selected site: left arm, course: TENS, mode: steady, time: 5 minutes. In this manner, the terminal device 10 swaps the treatment content Ta performed by the electrical treatment device 20A and the treatment content Tb performed by the electrical treatment device 20B.

Next, when the setting change via the internal processing described above is completed, the terminal device 10 displays a screen 1408 and instructs the electrical treatment devices 20A, 20B to resume the ceased treatment in accordance with the post-swap treatment content. Specifically, the terminal device 10 instructs the electrical treatment device 20B attached to the "left arm" to perform the post-swap treatment content Ta (i.e., the treatment content Tb prior to swapping). Also, the terminal device 10 instructs the electrical treatment device 20A attached to the "waist" to perform the post-swap treatment content Tb (i.e., the treatment content Ta prior to swapping).

Device Connection: Automatic

In the foregoing, the connection establishment with the device, treatment setting, and the series of operations during the treatment were described. Here, the operation flow when the terminal device 10 is automatically connected to the electrical treatment device 20 that has been paired with the terminal device 10 will be described.

Figure 10:
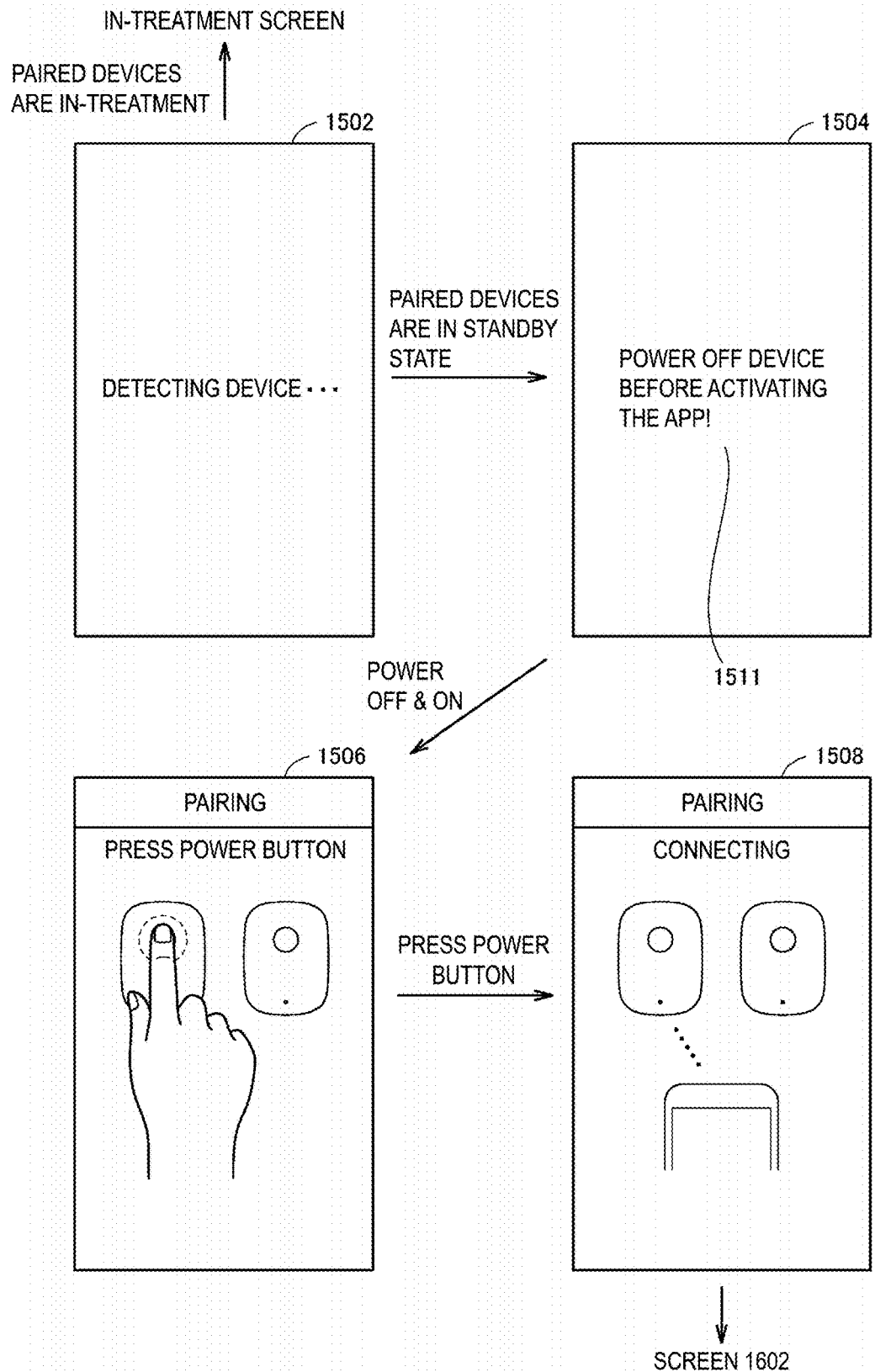
FIG. 10 is a screen transition diagram for explaining a flow of automatically connecting together the terminal device and the electrical treatment device.
Figure 11:
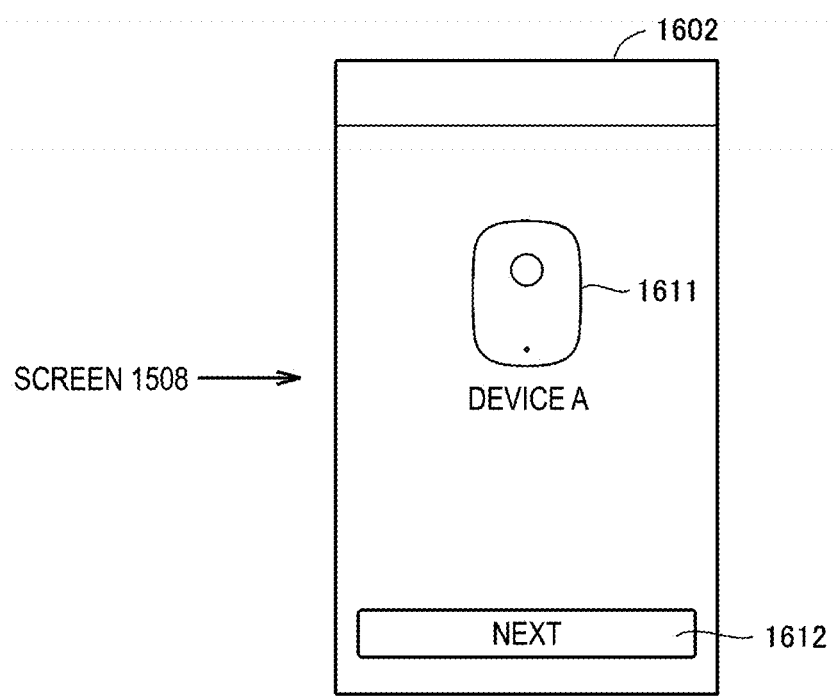
FIG. 11 is a screen transition diagram for explaining a flow of automatically connecting together the terminal device and the electrical treatment device.

FIGS. 10 and 11 are screen transition diagrams for explaining the flow of automatically connecting together the terminal device 10 and the electrical treatment device 20.

Referring to FIG. 10, the terminal device 10, receiving an instruction to activate the treatment app, displays after a splash screen a screen 1502 and detects the electrical treatment device 20 paired with the terminal device 10 via a scanning operation. The screen 1502 is a screen showing that the electrical treatment device 20 is being detected. When the paired electrical treatment device 20 is detected, the terminal device 10 connects to the detected electrical treatment device 20 and acquires state information from the electrical treatment device 20. At this point, the electrical treatment device 20 and the device on the treatment app screen are not associated.

The terminal device 10, on the basis of the acquired state information, displays a screen 1504 when it is determined that all of the paired electrical treatment devices 20 are in a standby state (treatment standby state) in which treatment is not being performed. Information 1511 prompting the user to turn the electrical treatment device 20 power OFF before activating the treatment app is displayed on the screen 1504. In addition, when it is determined that any one of the paired electrical treatment devices 20 is performing treatment (treating state), an in-treatment screen (for example, the screen 1402) is displayed. The reason why the information 1511 is displayed and the reason for transitioning to the in-treatment screen will be described later.

Once the paired electrical treatment device 20 is powered OFF then ON again, the terminal device 10 detects the electrical treatment device 20 via a scanning operation and displays a screen 1506. The screen 1506 is a screen that prompts for the paired first electrical treatment device 20 (for example, the electrical treatment device 20A) to be powered ON.

Next, when the power source of the electrical treatment device 20A is pressed down by the user in accordance with the screen 1506, the terminal device 10 displays a screen 1508 and begins the connection process with the electrical treatment device 20A. Then, the terminal device 10 establishes a connection with the electrical treatment device 20A and displays a screen 1602 illustrated in FIG. 11.

Referring to FIG. 11, the screen 1602 is a preparation screen for setting the treatment content Ta performed by the electrical treatment device 20A that has been connected with the terminal device 10. The electrical treatment device 20A is associated with the device A in the treatment app. Note that the device A corresponds to a device object 1611. Receiving selection of a button 1612 from the user in a state where the device object 1611 is selected, the terminal device 10 starts the flow of setting the treatment content Ta. For example, the screen 1602 transitions to the screen 1204.

The reason why the information 1511 is displayed will now be described. This is to prevent an operation flow in which the treatment app is activated and the treatment content is set, after the electrical treatment device 20 is powered ON and the electrical treatment device 20 is attached to a site on the body. Specifically, in the present embodiment, the terminal device 10 and the electrical treatment device 20 are wirelessly connected. Accordingly, the user is more likely to be confused about with which electrical treatment device 20 the device (and set treatment content) on the treatment app screen is associated, compared to a case where the terminal device 10 and the electrical treatment device 20 are wire-connected.

For example, when the treatment app is activated with the electrical treatment devices 20A, 20B powered ON, and a connection between the terminal device 10 and each device is established, the devices A, B on the treatment app screen are automatically associated with the electrical treatment devices 20A, 20B. This makes it difficult to determine with which electrical treatment device 20 the devices A, B on the treatment app screen is associated. The method of identification includes a method in which the LED of the electrical treatment device 20 is caused to flash (or light up, or the like) when the object of the device A or device B on the treatment app screen is tapped. However, if the electrical treatment device 20 is attached to the waist, back, or the like, it is difficult for the user to directly view the state of the LED after attachment.

To avoid a situation such as that described above, in the present embodiment, the terminal device 10 prompts for the electrical treatment device 20 to be powered OFF when the electrical treatment device 20, which has been detected when the treatment app is activated, is powered ON. With all the electrical treatment devices 20 powered OFF, the electrical treatment device 20 that has been detected first (in other words, powered ON first) is associated with the device A on the treatment app screen. This allows the user to easily know that the electrical treatment device 20 that the user powered ON first is associated with the device A on the treatment app screen.

However, in a case where either of the paired electrical treatment devices 20 is in a treating state, when the power is forcibly turned OFF, discomfort is caused to the user in treatment. Thus, in such a case, an in-treatment screen corresponding to the electrical treatment device 20 performing treatment is displayed.

Error Notification

Here, various types of error notifications executed by the terminal device 10 will be described.

Figure 12:
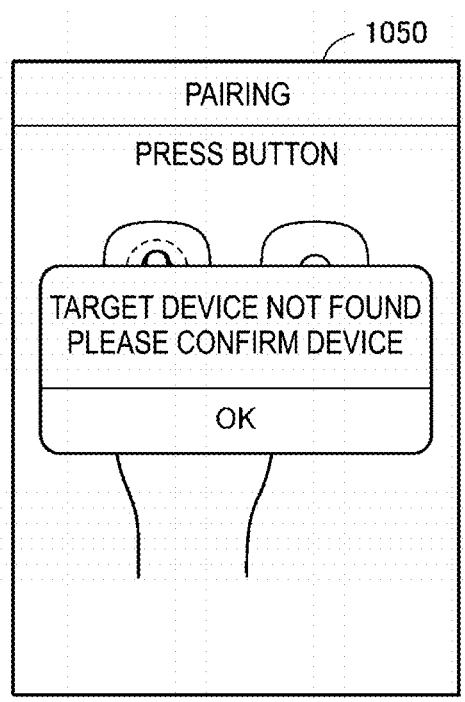
FIG. 12 is a diagram illustrating an example of an error notification.

FIG. 12 is a diagram illustrating an example of an error notification. Here, a case is assumed where the terminal device 10 is not paired with any electrical treatment device 20. In this case, the terminal device 10, receiving an instruction to activate the treatment app, displays after a splash screen the screen 1002 and starts a scan (see FIG. 5). If the terminal device 10, after scanning for a predetermined amount of time (for example, 180 seconds), cannot detect an advertisement including a device ID that satisfies a preset condition, the terminal device 10 displays a screen 1050 illustrated in FIG. 12.

The screen 1050 is a screen that prompts for confirmation of a state of the electrical treatment device 20 because the electrical treatment device 20 to be paired has not been found. Examples of a cause of such an error include the electrical treatment device 20 not being powered ON within a predetermined amount of time, the terminal device 10 and the electrical treatment device 20 being too far away from each other to detect the advertisement, and the like. Note that the terminal device 10 may be configured to provide notification on such a cause of error.

Figure 13:
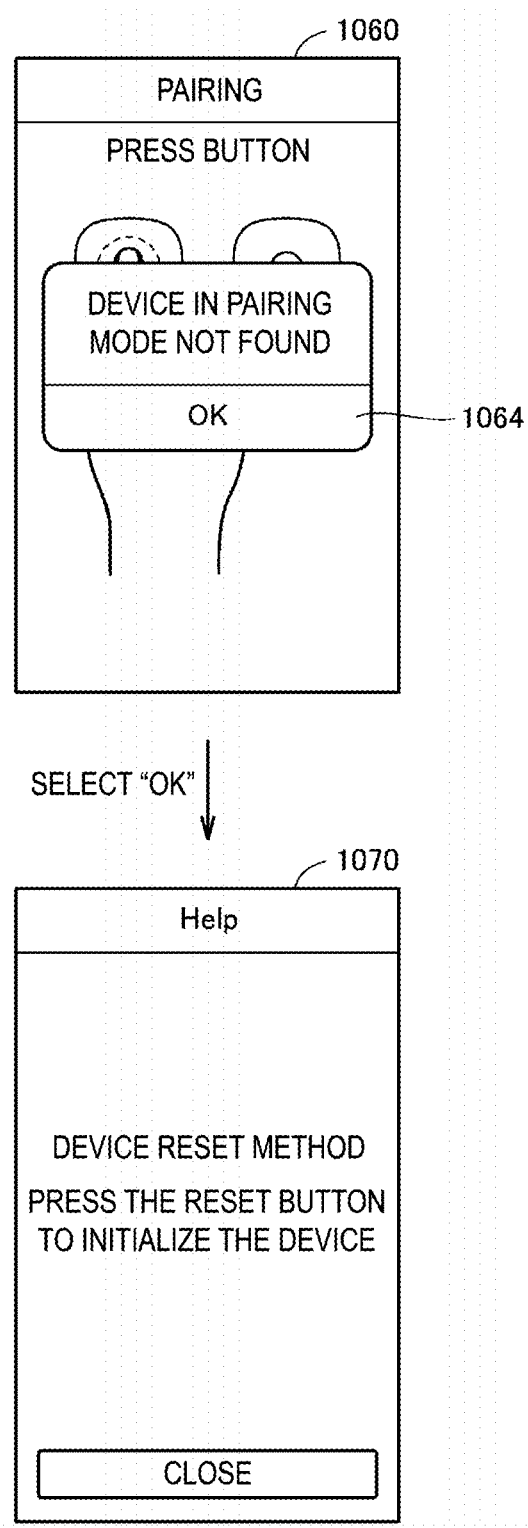
FIG. 13 is a diagram illustrating another example of an error notification.

FIG. 13 is a diagram illustrating another example of an error notification. Here again, a case is assumed where the terminal device 10 is not paired with any electrical treatment device 20. In this case, the terminal device 10 performs a scan for a predetermined amount of time (see the screen 1002 in FIG. 5) and detects an advertisement including a connection request mode, but does not detect an advertisement including a pairing request mode. In this case, the terminal device 10 issues an error notification saying that an electrical treatment device 20 in pairing request mode was not found, as illustrated in a screen 1060. Receiving selection of an OK button 1064, the terminal device 10 displays a screen 1070 that prompts for a reset button provided on the electrical treatment device 20 to be pressed in order to initialize the electrical treatment device 20.

Here, as described above, the electrical treatment device 20 is configured such that only the pairing information of one BLE device can be stored in the internal memory. Thus, if pairing information is stored in the internal memory, the electrical treatment device 20 operates in the connection request mode, and if pairing information is not stored in the internal memory, the electrical treatment device 20 operates in pairing request mode.

This means that the electrical treatment device 20 from which the advertisement including the connection request mode was emitted is paired with a BLE device other than the terminal device 10 and pairing information of this other BLE device is stored therein. Accordingly, to pair with the terminal device 10, the existing pairing information of the electrical treatment device 20 needs to be deleted. Thus, the terminal device 10 displays the screen 1070 and causes the pairing information stored in the electrical treatment device 20 to be deleted.

Figure 14:
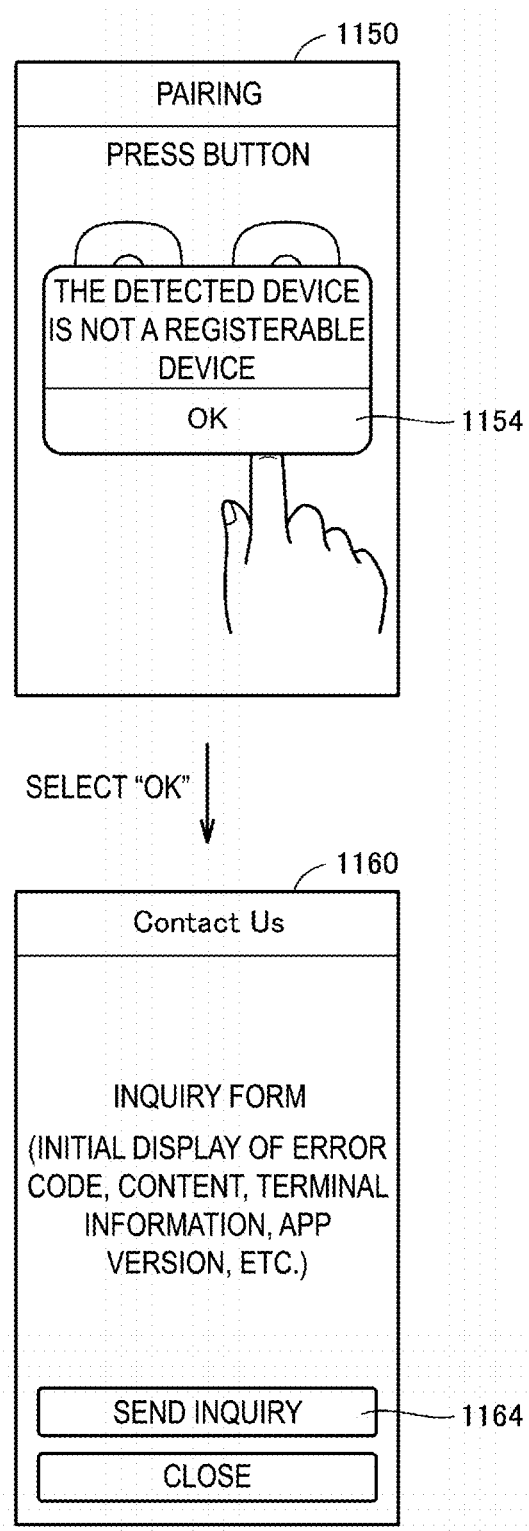
FIG. 14 is a diagram illustrating still another example of an error notification.

FIG. 14 is a diagram illustrating still another example of an error notification. Here, a case is assumed where the terminal device 10 has paired with the first electrical treatment device 20 and attempts to pair with the second electrical treatment device 20. First, referring to the screen 1104 in FIG. 6, when the power source of the second electrical treatment device 20 is pressed down by the user in accordance with the screen 1102, the terminal device 10 begins the connection process with the electrical treatment device 20. The terminal device 10 detects, via the scanning operation, an advertisement emitted from the second electrical treatment device 20.

Then, in a case where classification information Ca of the device ID included in the advertisement does not match classification information Cb of the device ID of the first paired electrical treatment device 20, the terminal device 10 issues an error notification saying that the second electrical treatment device 20 cannot be registered, as illustrated on a screen 1150. For example, the electrical treatment device 20 may be assigned different classification information for each sale area. Thus, in a case where the sale area of the second electrical treatment device 20 is different from the sale area of the registered first electrical treatment device 20, a notification is issued saying that the second electrical treatment device 20 cannot be registered. In addition, the electrical treatment device 20 may be assigned different classification information for each device model. In this case, if the model of the second electrical treatment device 20 is different from the model of the registered first electrical treatment device 20, a notification is issued saying that the second electrical treatment device 20 cannot be registered.

Receiving selection of an OK button 1154, the terminal device 10 displays a screen 1160 showing an inquiry form. For example, the screen 1160 is provided with an error code, error content, terminal information, app version, a field for filling out inquiry details, and the like. When the terminal device 10 receives selection of an inquiry send button 1164, the terminal device 10 transmits to a predetermined external device the details that have been input.

Functional Configuration

Figure 15:
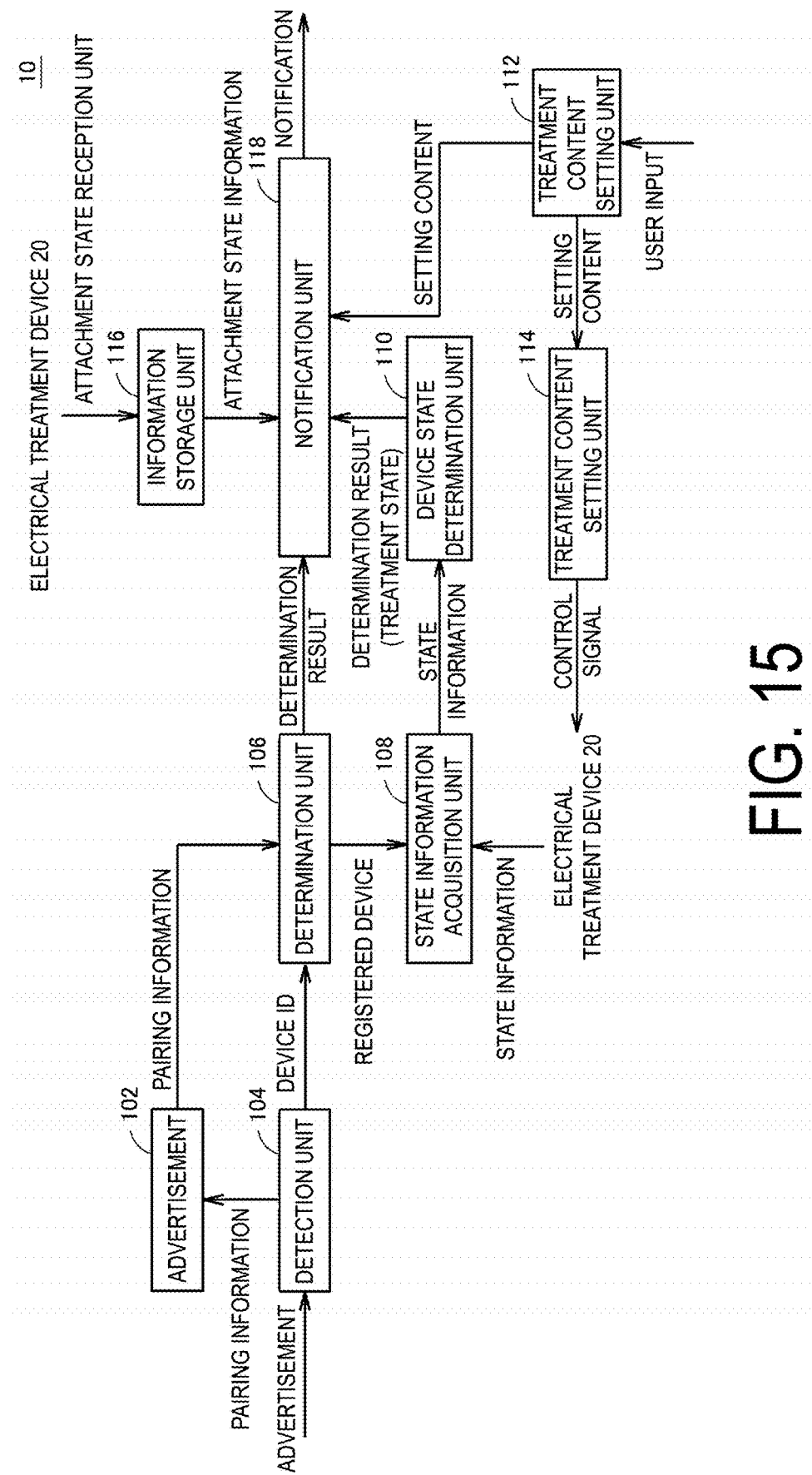
FIG. 15 is a block diagram illustrating an example of a functional configuration of the terminal device.

FIG. 15 is a block diagram illustrating an example of a functional configuration of the terminal device 10. Referring to FIG. 15, the terminal device 10 includes, as main components, a detection unit 104, a determination unit 106, a state information acquisition unit 108, a device state determination unit 110, a treatment content setting unit 112, a treatment instruction unit 114, an attachment state reception unit 116, and a notification unit 118. Each function of the terminal device 10 is realized, for example, by the processor 152 of the terminal device 10 executing a program stored in the memory 154. Note that one or more or all of these functions may be configured to be realized by hardware. The terminal device 10 further includes an information storage unit 102 realized by the memory 154.

The information storage unit 102 stores registration information for establishing a wireless communication connection with at least one of the electrical treatment devices 20. Typically, the registration information is pairing information and includes device ID, MAC address, service information, and the like of the paired electrical treatment device 20.

The detection unit 104 detects a beacon signal emitted from at least one of the electrical treatment devices 20. Specifically, the detection unit 104 detects, via the scanning operation, an advertisement including the device ID having type information indicating "electrical treatment device". When the pairing request is received, the detection unit 104 stores in the information storage unit 102 the pairing information included in the detected advertisement.

The determination unit 106 determines, on the basis of the pairing information stored in the information storage unit 102 and the advertisement detected by the detection unit 104, whether an unregistered electrical treatment device 20, which has not been registered with the terminal device 10, is present among the detected electrical treatment devices 20. Specifically, in a case where pairing information that matches the pairing information included in the advertisement is stored in the information storage unit 102, the determination unit 106 determines that the electrical treatment device 20 that emitted the advertisement is registered with the terminal device 10. In a case where pairing information that matches the pairing information included in the advertisement is not stored in the information storage unit 102, the determination unit 106 determines that the electrical treatment device 20 that emitted the advertisement is not registered (in other words, is unregistered) with the terminal device 10.

In a case of the unregistered electrical treatment device 20 being present, the determination unit 106 further determines whether the unregistered electrical treatment device 20 includes pairing information of a device other than the terminal device 10. Specifically, if the unregistered electrical treatment device 20 is emitting an advertisement including a connection request to establish a wireless communication connection, then the determination unit 106 determines that the unregistered electrical treatment device 20 includes registration information of another device.

According to another aspect, the determination unit 106 further determines, on the basis of the detected advertisement, whether classification (classification determined by the classification information Ca) to which the unregistered electrical treatment device 20 belongs and classification (classification determined by the classification information Cb) to which the electrical treatment device 20 registered with the terminal device 10 belongs are the same.

The state information acquisition unit 108 acquires state information of the electrical treatment device 20 from the electrical treatment device 20 determined to be registered with the terminal device 10 by the determination unit 106. Specifically, after a wireless communication connection is established with the electrical treatment unit 20 registered with the terminal device 10, the state information acquisition unit 108 receives state information from the electrical treatment device 20. The state information includes information indicating whether the registered electrical treatment device 20 is in an in-treatment state or a treatment standby state in which treatment is not being performed.

The device state determination unit 110 determines, on the basis of the state information of the electrical treatment devices 20A, 20B, whether the electrical treatment devices 20A, 20B are each in an in-treatment state or a treatment standby state.

The treatment content setting unit 112 sets the treatment content Ta performed by the electrical treatment device 20A and the treatment content Tb performed by the electrical treatment device 20B. The treatment content includes a treatment site, a treatment course, a treatment mode, and a treatment time. Also, in an aspect, the treatment content setting unit 112 swaps the treatment content Ta and the treatment content Tb in accordance with a preset instruction (for example, selection of the SWAP button 1424).

The treatment instruction unit 114 instructs the electrical treatment devices 20A, 20B to treat in accordance with the treatment contents Ta, Tb. Specifically, the treatment instruction unit 114 sends to each electrical treatment device 20A, 20B a control signal causing each treatment content Ta, Tb to be performed. In addition, the treatment instruction unit 114 sends various control signals to each electrical treatment device 20A, 20B in accordance with various instructions from the user (for example, a stimulation level change instruction, a treatment stop instruction, and the like).

In an aspect, when the treatment content Ta and the treatment content Tb are swapped, the treatment instruction unit 114 instructs the electrical treatment devices 20A, 20B to treat the user in accordance with the post-swap treatment content Ta (the treatment content Tb prior to swapping) and the post-swap treatment content Tb (the treatment content Ta prior to swapping).

The attachment state reception unit 116 receives attachment state information indicating a state of attachment of the pad 2 to the user from each electrical treatment device 20A, 20B. The attachment state information is information indicating whether the pad 2 is attached to the user or is not attached (peeled off).

The notification unit 118 notifies the user of various information. Typically, the notification unit 118 issues notifications by causing the display 158 to display various types of information.

In an aspect, the notification unit 118 issues a notification of information including a solution for an error when the electrical treatment device 20 not registered with the terminal device 10 includes the pairing information of another device. For example, the notification unit 118 issues, as a way to solve the error, a notification (displayed on the screen 1070, for example) to perform a predetermined operation (for example, press down a reset button) using hardware (for example, a physical switch, a button, or the like) provided on the unregistered electrical treatment device 20. When a reset button provided on the unregistered electrical treatment device 20 is pressed down by the user, the pairing information of other devices stored in the unregistered electrical treatment device 20 is deleted. Note that in a case of multiple solutions existing for the error, the notification unit 118 may display a list of solutions on the display 158.

In another aspect, in a case where classification to which the unregistered electrical treatment device 20 belongs does not match classification to which the registered electrical treatment device 20 belongs, the notification unit 118 issues a notification saying that the unregistered electrical treatment device 20 will not be registered. For example, the electrical treatment device 20 may be assigned different classification information for each sale area (or model). Thus, if the sale area (or model) of the unregistered electrical treatment device 20 is different from the sale area (or model) of the registered electrical treatment device 20, the notification unit 118 issues a notification saying that the unregistered electrical treatment device 20 will not be registered.

In still another aspect, when the electrical treatment device 20A and the electrical treatment device 20B are determined by the device status determination unit 110 to be in a treatment standby state, the notification unit 118 issues a notification to power OFF the electrical treatment device 20A and the electrical treatment device 20B. In addition, in a case where at least one of the electrical treatment device 20A and the electrical treatment device 20B is in an in-treatment state, the notification unit 118 causes the display 158 of the terminal device 10 to display a treatment screen corresponding to the electrical treatment device 20 in the in-treatment state.

In yet another aspect, when the state of attachment of the pad 2 to the user is determined to be changed on the basis of the attachment state information, the notification unit 118 provides notification on the change of the attachment state. Specifically, in a case where a state of the pad 2 is changed, i.e., from a state of being not attached to the user to a state of being attached to the user, the notification unit 118 notifies the user that the pad 2 has been attached. In addition, in a case where a state of the pad 2 is changed, i.e., from a state of being attached to the user to a state of being peeled off, the notification unit 118 notifies the user that the pad 2 has been peeled off.

Processing Procedure

Figure 17:
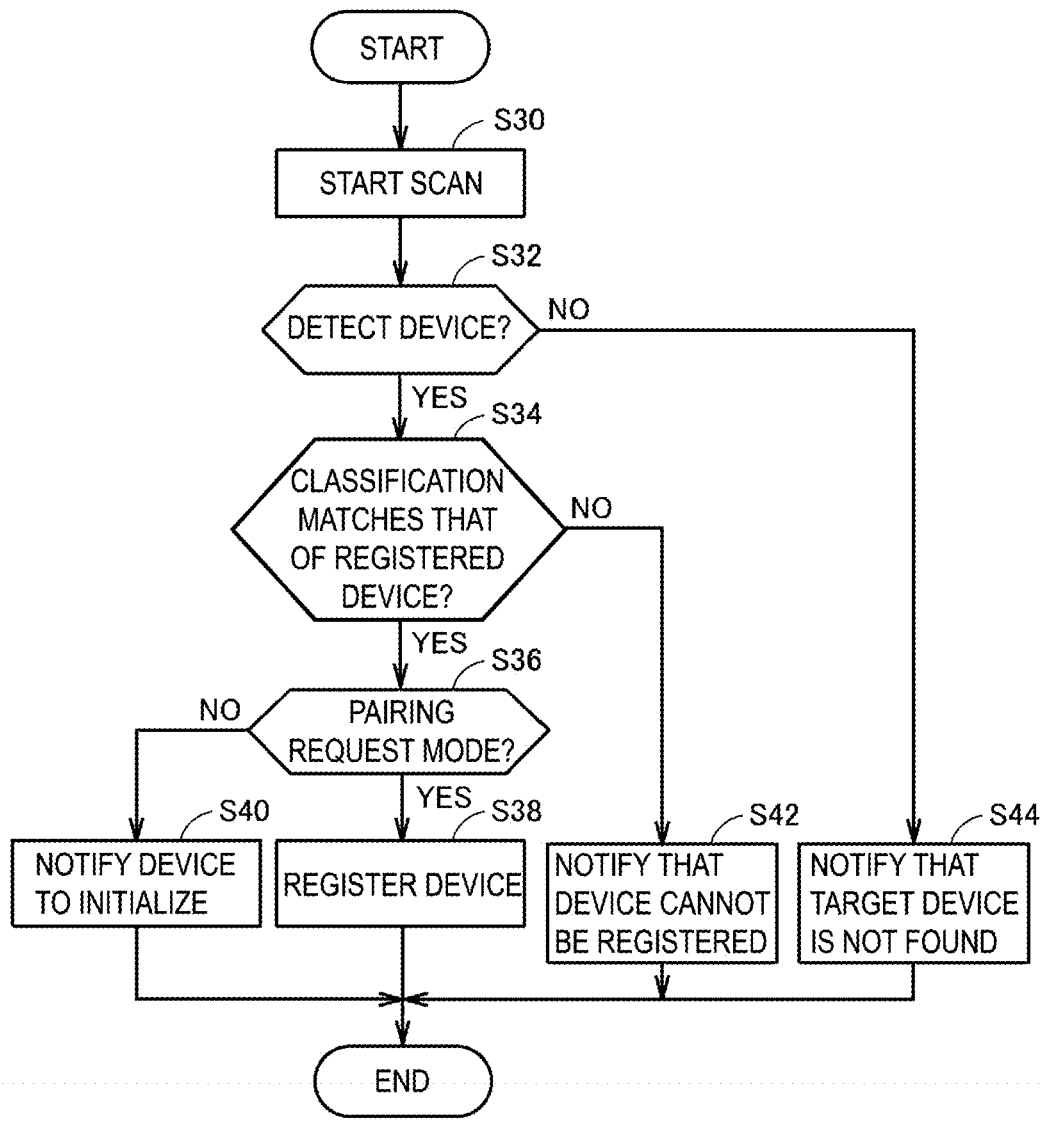
FIG. 17 is a flowchart illustrating another example of a processing procedure for device registration by the terminal device.
Figure 18:
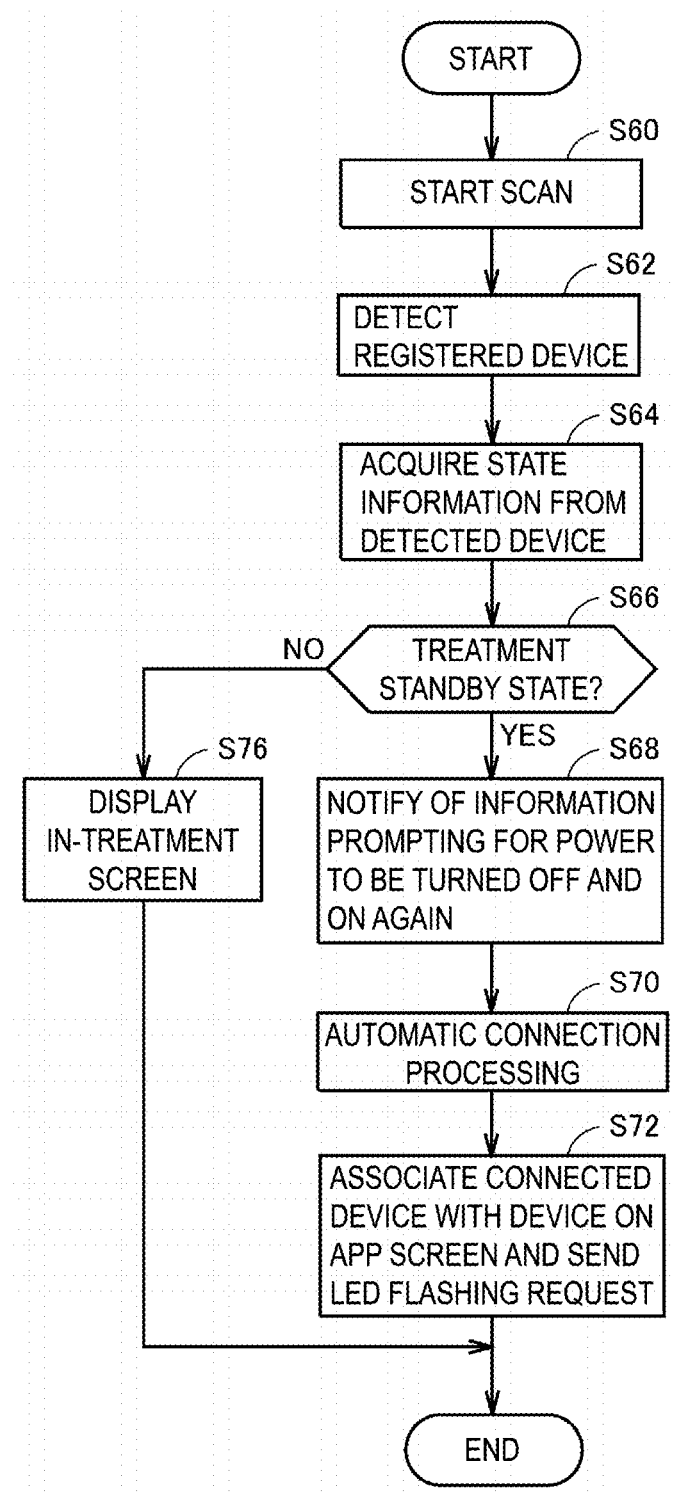
FIG. 18 is a flowchart illustrating an example of a processing procedure for normal connection by the terminal device.

Various types of processing procedures executed by the terminal device 10 according to the present embodiment will be described with reference to FIGS. 16 to 18. Steps illustrated in FIGS. 16 to 18 are realized mainly by the processor 152 of the terminal device 10 executing a program (treatment app) stored in the memory 154.

Device Registration

Figure 16:
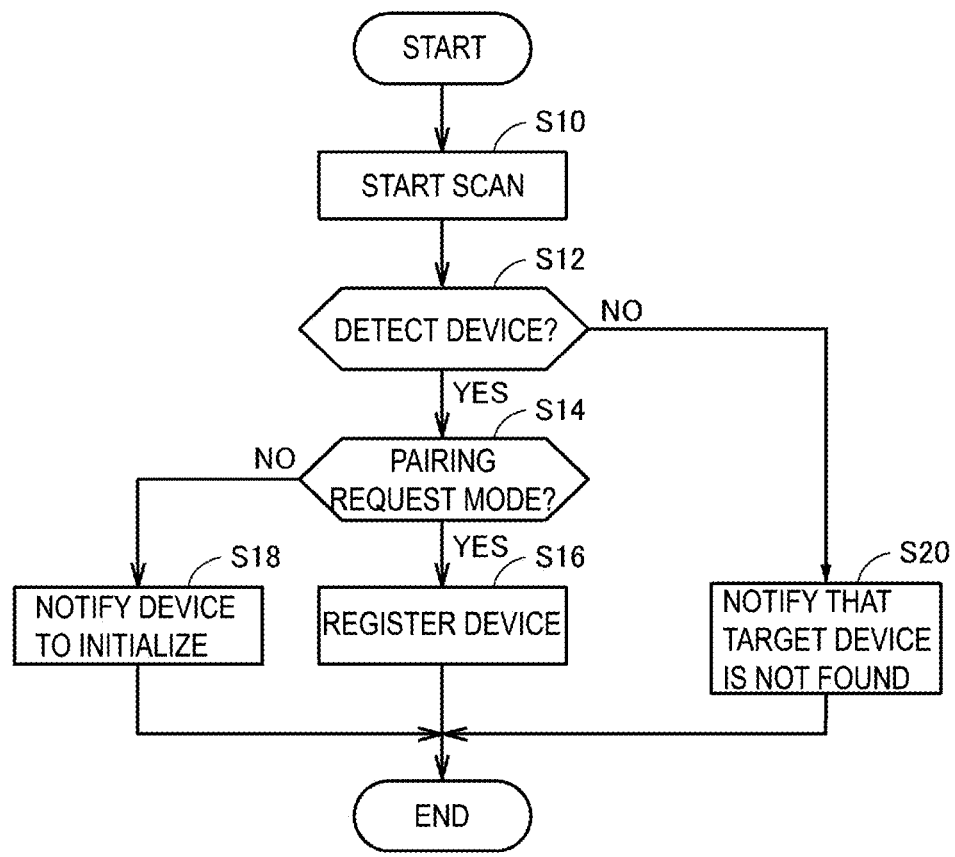
FIG. 16 is a flowchart illustrating an example of a processing procedure for device registration by the terminal device.

FIG. 16 is a flowchart illustrating an example of a processing procedure for device registration by the terminal device 10. Here, a case is assumed where the terminal device 10 attempts to register the first electrical treatment device 20.

Referring to FIG. 16, the terminal device 10 begins a scanning operation (step S10) and determines whether the advertisement emitted from the electrical treatment device 20 has been detected within a predetermined amount of time (step S12). When no electrical treatment device 20 is detected (NO in step S12), the terminal device 10 notifies that the electrical treatment device 20 to be paired has not been found (see FIG. 12) (step S20). Then the process ends. When the electrical treatment device 20 is detected (YES in step S12), the terminal device 10 determines whether the operating mode of the electrical treatment device 20 emitting the advertisement is in a pairing request mode (step S14).

When the operating mode is the pairing request mode (YES in step S14), the terminal device 10 registers the pairing information of the electrical treatment device 20 (step S16) and establishes a wireless connection, and the process ends. At this time, the electrical treatment device 20 registers the pairing information of the terminal device 10. However, when the operating mode is not in the pairing request mode (that is, the connection request mode) (NO in step S14), the terminal device 10 issues a notification to initialize the electrical treatment device 20 (see FIG. 13) (step S18), and the process ends. Specifically, the terminal device 10 issues a notification to press the reset button of the electrical treatment device 20 and delete the pairing information.

FIG. 17 is a flowchart illustrating another example of a processing procedure for device registration by the terminal device 10. Here, a case is assumed where the terminal device 10 attempts to register the second electrical treatment device 20 with the first electrical treatment device 20 being registered.

Referring to FIG. 17, the process including steps S30, S32, and S44 is same as the process including steps S10, S12, and S20 of FIG. 16, and thus the detailed description thereof is not repeated. When the electrical treatment device 20 is detected (YES in step S32), the terminal device 10 determines whether classification to which the detected electrical treatment device 20 belongs matches the classification to which registered electrical treatment device 20 belongs (step S34).

When these classifications do not match (NO in step S34), the terminal device 10 notifies that the detected electrical treatment device 20 is not a registerable device (see FIG. 14) (step S42), and the process ends. When these classifications match (YES in step S34), the terminal device 10 performs the processing of step S36. The process including steps S36, S38, and S40 is same as the process including steps S14, S16, and S18 of FIG. 16, and thus the detailed description thereof is not repeated.

Connection Establishment

FIG. 18 is a flowchart illustrating an example of a processing procedure for normal connection by the terminal device 10. Here, a case is assumed where the terminal device 10 attempts to establish a wireless connection with the registered electrical treatment device 20.

Referring to FIG. 18, the terminal device 10 begins a scanning operation (step S60) and detects the registered electrical treatment device 20 (step S62). The terminal device 10 acquires a state information from the detected electrical treatment device 20 (step S64) and determines whether the electrical treatment device 20 is in a treatment standby state on the basis of the state information (step S66).

When the electrical treatment device 20 is not in a treatment standby state (in other words, is in an in-treatment state) (NO in step S66), the terminal device 10 displays on the display 158 an in-treatment screen corresponding to the electrical treatment device 20 (step S76), and the process ends. When the electrical treatment device 20 is in the treatment standby state (YES in step S66), a notification is issued of information prompting for the power to be turned OFF then ON again (see FIG. 10) (step S68).

Then, the terminal device 10 automatically establishes a wireless communication connection with the electrical treatment device 20 powered back ON (step S70). The terminal device 10 associates the connected electrical treatment device 20 with the device on the treatment app screen and sends an LED flash request to the electrical treatment device 20 (step S72), and the process ends.

Advantages

According to the present embodiment, the pairing information of only one BLE device can be registered in the electrical treatment device 20. With communication with devices other than the one registered BLE device being effectively blocked, this allows the user of the terminal device 10 to receive a highly safe treatment in accordance with the user's intended treatment content, without the control of the electrical treatment device 20 taken over. In addition, when the pairing information of another device is already registered with the electrical treatment device 20, a notification of a solution for the error is issued from the terminal device 10, so that the user can easily know the procedure for completing the pairing. In addition, because pairing information can be deleted using the reset button provided on the electrical treatment device 20, the pairing information can be easily deleted.

According to the present embodiment, the user can easily know which electrical treatment device 20 corresponds to the device the user selected on the treatment app screen. Also, when treatment is performed using two electrical treatment devices, the SWAP button can be utilized to easily swap the treatment contents corresponding to the electrical treatment devices, even if the devices on the treatment app screen and the electrical treatment devices, i.e., actual devices, are associated in a manner different from how the user perceived. Thus, a cumbersome task such as reattaching the electrical treatment devices does not need to be performed.

In the present embodiment, the terminal device 10 is configured to provide notifications of various types of error information and information that prompts for work procedures. Thus, the user can easily perform a series of operations, which ranges from establishing a connection between the terminal device 10 and the electrical treatment device 20 to the setting of the treatment content and the performance of the treatment.

Other Embodiments (1) In the embodiment described above, a configuration has been described in which, when the SWAP button 1424 is selected, all of the treatment content Ta and all of the treatment content Tb are swapped, but the configuration is not limited thereto. For example, a configuration may be employed in which a portion of the treatment content Ta and a portion of the treatment content Tb are swapped. Specifically, the "mode" in the treatment content Ta and the "mode" in the treatment content Tb may be swapped, or the "stimulation level" in the treatment content Ta and the "stimulation level" in the treatment content Tb may be swapped. In such a configuration, when the SWAP button 1424 is selected, the user may be asked to select which item (for example, "mode" or "stimulation level") of the treatment content the user swaps.

(2) In the embodiment described above, a configuration has been described in which the terminal device 10 wirelessly communicates with the electrical treatment devices 20A, 20B, but the configuration is not limited thereto. For example, the terminal device 10 may be capable of wireless communication with only one of the electrical treatment devices 20 (for example, the electrical treatment device 20A), and the one electrical treatment device 20A may be capable of wireless communicate with the other electrical treatment device 20 (for example, electrical treatment device 20B). Specifically, the electrical treatment device 20A, which is capable of wireless communication with the terminal device 10, operates as a "master device", and the electrical treatment device 20B, which is capable of wireless communication with the master device, operates as a "slave device".

In this case, the terminal device 10 directly provides various instructions to the master device, and the slave device is indirectly provided with various instructions via the master device. The master device controls the slave device in accordance with instructions from the terminal device 10.

In an aspect, the terminal device 10 (treatment instruction unit 114) instructs the master device to treat a user in accordance with the treatment content Ta. In addition, the treatment instruction unit 114 causes the master device to control the slave device to treat the user in accordance with the treatment content Tb. Specifically, the treatment instruction unit 114 sends a control signal to the master device to cause the treatment content Ta to be performed. The treatment instruction unit 114 sends a control signal to the master device to cause the treatment content Tb to be performed, and the master device controls the slave device via the control signal being transferred to the slave device.

In another aspect, when the treatment content Ta and the treatment content Tb are swapped, the treatment instruction unit 114 instructs the master device to treat the user in accordance with the post-swap treatment content Ta and causes the master device to control the slave device to treat the user in accordance with the post-swap treatment content Tb.

The terminal device 10 (state information acquisition unit 108) receives the state information of the master device from the master device and receives the state information of the slave device via the master device. The terminal device 10 (attachment state reception unit 116) receives the attachment state information of the pad 2 corresponding to the master device and receives the attachment state information of the pad 2 corresponding to the slave device via the master device. In other words, the master device receives various information from the slave device and transfers the same to the terminal device 10.

In the case of the configuration described above, the terminal device 10 only needs to be paired and connected with one electrical treatment device, and this makes it possible to omit the work of pairing multiple electrical treatment devices. In addition, because the slave device is controlled by the master device after the terminal device 10 has provided various instructions to the master device, it becomes easier to implement a synchronization of the timing and the like of the treatment between the master instrument and the slave device.

(3) In the embodiments described above, a program may be provided that causes a computer to function and execute controls such as those described in the flowcharts described above. Such a program can also be provided as a program product stored on a non-temporary computer-readable recording medium, such as a flexible disk, a compact disk read only memory (CD), a secondary storage device, a main storage device, a memory card, and the like attached to a computer. Alternatively, a program may be provided, which is stored on a recording medium such as a hard disk built into a computer. The program may also be provided by download via a network.

With the program, required modules from among program modules provided as part of the computer operating system (OS) may be called in a predetermined sequence at a predetermined timing to execute processing. In this case, the modules described above are not included in the program itself, and the process is executed in cooperation with the OS. Programs that do not include such modules may also be included in the program according to the present embodiment.

In addition, the program according to the present embodiment may be provided integrated into a part of another program. In this case as well, the modules included in the other programs described above are not included in the program itself, and the process is executed in cooperation with the other programs. Programs included in such other programs may also be included in the program according to the present embodiment.

(4) The configuration given as an example of the embodiment described above is an example configuration of the present invention. The configuration can be combined with other known technology, and parts thereof may be omitted or modified within the scope of the present invention. Furthermore, the processes and configurations of other embodiments may be employed as appropriate to the embodiments described above.

The embodiments described herein are illustrative in all respects and are not intended as limitations. The scope of the present invention is indicated not by the descriptions above but by the claims and includes all meaning equivalent to the scope and changes within the scope.

REFERENCE SIGNS LIST

1 Treatment system
2 Pad
2H Through hole
2X Attachment portion
2Y Treatment portion
2a Conductive layer
3 Holder
4 Body portion
4a Case
5 Guiding/engagement portion
10 Terminal device
20 Electrical treatment device
21 Body-side portion
22 Pad side electrode portion
23 Window portion
30 Network
31 Pad holding portion
32 Wall portion
33 Interlock pin
41 Side surface
43 Main body portion side electrode portion
48S Switch
51 Protrusion
52 Groove portion
102 Information storage unit
104 Detection unit
106 Determination unit
108 State information acquisition unit
110 Device state determination unit
112 Treatment content setting unit
114 Treatment instruction unit
116 Attachment state reception unit
118 Notification unit
152 Processor
154 Memory
156 Input device
158 Display
160 Wireless communication unit 162 Communication antenna
164 Memory interface
165 Storage medium
168 Speaker
170 Microphone
311 Upper surface
312 Positioning protrusion
521 Vertical groove portion
522 Lateral groove portion

The invention claimed is:

1. A terminal device configured to wirelessly communicate with at least one electrical treatment device, comprising:
   an information storage configured to store registration information by which a wireless communication connection with the at least one electrical treatment device is established;
   wireless communication circuitry configured to detect a beacon signal emitted from the at least one electrical treatment device; and
   a processor configured to:
      determine, on the basis of the registration information stored in the information storage and the beacon signal that is detected, whether the at least one electrical treatment device includes an unregistered electrical treatment device not registered with the terminal device, wherein
   when the unregistered electrical treatment device is included, the processor is further configured to determine, on the basis of the beacon signal that is detected, whether the unregistered electrical treatment device comprises registration information of a device other than the terminal device,
   wherein the processor is further configured to provide notification on information comprising a solution for an error, when the unregistered electrical treatment device comprises the registration information of the device other than the terminal device.

2. The terminal device according to claim 1, wherein when the unregistered electrical treatment device is emitting the beacon signal comprising a connection request for establishing the wireless communication connection, the processor is further configured to determine that the unregistered electrical treatment device comprises the registration information of the device other than the terminal device.

3. The terminal device according to claim 1, wherein the processor is further configured to:
   determine, on the basis of the beacon signal that is detected, whether a first classification to which the unregistered electrical treatment device belongs matches a second classification to which the at least one electrical treatment device registered with the terminal device belongs; and
   notify that the unregistered electrical treatment device will not be registered, when the first classification and the second classification do not match.

4. The terminal device according to claim 1, wherein the processor is further configured to acquire state information of the at least one treatment device, which has been determined to be registered with the terminal device, from the electrical treatment device determined to be registered with the terminal device, wherein
   the state information comprises information indicating whether the registered electrical treatment device is in an in-treatment state or a treatment standby state in which the registered electrical treatment device is not in the in-treatment state; and
   when the electrical treatment device is in the treatment standby state, the processor is further configured to provide notification to power OFF the electrical treatment device.

5. The terminal device according to claim 1, wherein the processor is further configured to provide notification on hardware, which is provided on the unregistered electrical treatment device, to be used to perform a predetermined operation for the solution.

6. The terminal device according to claim 1,
   wherein the registration information stored in the information storage includes pairing information for each of the at least one electrical treatment devices; and
   wherein the processor is further configured to:
      identify, from the beacon signal, pairing information for the at least one electrical treatment device;
      compare the pairing information from the beacon signal with the pairing information stored in the information storage; and
      determine that the at least one electrical treatment device is not registered with the terminal device based on the comparison of the pairing information from the beacon signal with the pairing information stored in the information storage.

7. A treatment system, comprising:
   at least one electrical treatment device; and
   a terminal device configured to wirelessly communicate, via wireless communication circuitry, with the at least one electrical treatment device and detect a beacon signal emitted from the at least one electrical treatment device, wherein
   the terminal device comprises a processor configured to:
      store registration information by which a wireless communication connection with the at least one electrical treatment device is established;
      determine, based on the registration information stored in the information storage and the beacon signal that is detected, whether the at least one electrical treatment device includes an unregistered electrical treatment device not registered with the terminal device, and
   when the unregistered electrical treatment device is included, the processor is further configured to determine, based on the beacon signal that is detected, whether the unregistered electrical treatment device comprises registration information of a device other than the terminal device,
   wherein the processor is further configured to provide notification on information comprising a solution for an error, when the unregistered electrical treatment device comprises the registration information of the device other than the terminal device.

8. A non-transitory recording medium that stores a program executed by a computer of a terminal device configured to wirelessly communicate with at least one electrical treatment device, the terminal device comprising a memory configured to store registration information by which a wireless communication connection with the at least one electrical treatment device is established, the program causing the computer to execute:
   determining that a beacon signal emitted from the at least one electrical treatment device has been detected;
   determining, based on the registration information stored in the memory and the beacon signal that has been detected, whether the at least one electrical treatment device includes an unregistered electrical treatment device not registered with the terminal device;

when the unregistered electrical treatment device is included, determining, based on the beacon signal that has been detected, whether the unregistered electrical treatment device comprises registration information of a device other than the terminal device; and providing notification on information comprising a solution for an error, when the unregistered electrical treatment device comprises the registration information of the device other than the terminal device.

* * * * *